United States Patent
Takahashi et al.

(10) Patent No.: US 9,222,947 B2
(45) Date of Patent: Dec. 29, 2015

(54) ANTI-SAPPβ ANTIBODY

(71) Applicant: SHIONOGI & CO., LTD., Osaka-shi, Osaka (JP)

(72) Inventors: Tatsuya Takahashi, Toyonaka (JP); Junji Onoda, Toyonaka (JP); Yasunobu Yoshida, Sapporo (JP); Shoji Yamane, Toyonaka (JP); Kouhei Nishitomi, Toyonaka (JP); Hidekuni Yamakawa, Toyonaka (JP); Akira Yamauchi, Toyonaka (JP); Atsushi Morita, Toyonaka (JP); Isao Fukuda, Toyonaka (JP)

(73) Assignee: SHIONOGI & CO., LTD., Osaka-shi, Osaka ( * ) Notice: Subject to any disclaimer, the term of this patent is extended or adjusted under 35 U.S.C. 154(b) by 0 days.

(21) Appl. No.: 14/376,305

(22) PCT Filed: Feb. 1, 2013

(86) PCT No.: PCT/JP2013/052317
§ 371 (c)(1),
(2) Date: Aug. 1, 2014

(87) PCT Pub. No.: WO2013/115348
PCT Pub. Date: Aug. 8, 2013

(65) Prior Publication Data
US 2015/0111231 A1    Apr. 23, 2015

(30) Foreign Application Priority Data

Feb. 3, 2012 (JP) .................................. 2012-021431

(51) Int. Cl.
*C07K 16/18* (2006.01)
*C07K 7/04* (2006.01)
*C12P 21/08* (2006.01)
*G01N 33/536* (2006.01)
*G01N 33/53* (2006.01)
*G01N 33/15* (2006.01)
*G01N 33/68* (2006.01)

(52) U.S. Cl.
CPC ............ *G01N 33/6896* (2013.01); *C07K 16/18* (2013.01); *C07K 2317/30* (2013.01); *C07K 2317/565* (2013.01); *G01N 2333/47* (2013.01); *G01N 2333/4709* (2013.01); *G01N 2333/96475* (2013.01); *G01N 2500/00* (2013.01); *G01N 2800/28* (2013.01)

(58) Field of Classification Search
None
See application file for complete search history.

(56) References Cited

FOREIGN PATENT DOCUMENTS

| JP | 7-506967 A | 8/1995 |
|---|---|---|
| WO | WO 93/21526 A1 | 10/1993 |

(Continued)

OTHER PUBLICATIONS

Braak et al.,"Demonstration of Amyloid Deposits and Neurofibrillary Changes in Whole Brain Sections," Brain Pathology, vol. 1, 119, 1991, pp. 213-216.

(Continued)

*Primary Examiner* — Gregory S Emch
*Assistant Examiner* — Aurora M Fontainhas
(74) *Attorney, Agent, or Firm* — Birch, Stewart, Kolasch & Birch, LLP

(57) ABSTRACT

Provided are a monoclonal antibody capable of specifically recognizing a specific region of sAPP β or a fragment of said antibody and an assay method and an assay kit using the same, in order to accurately assay sAPPβ contained in a biological sample.

11 Claims, 12 Drawing Sheets

(56) References Cited

FOREIGN PATENT DOCUMENTS

| WO | WO 2008/008463 | A2 | 1/2008 |
|----|----|----|----|
| WO | WO 2010/046332 | A1 | 4/2010 |
| WO | WO 2010/079340 | A2 | 7/2010 |
| WO | WO 2010/079340 | A3 | 7/2010 |

OTHER PUBLICATIONS

Chapman et al., "Dementia and Its Implications for Public Health," Centers for Disease Control and Prevention, Preventing Chronic Desease, Public Health Research, Practice, and Policy, vol. 3, No. 2, Apr. 2006, pp. 1-13.

Jefferson et al., "Metalloprotease Meprin β Generates Nontoxic N-terminal Amyloid Precursor Protein Fragments in Vivo," The Journal of Biological Chemistry, vol. 286, No. 31, Aug. 5, 2011, pp. 27741-27750.

Le Brocque et al., "Processing of the Alzheimer's Disease Amyloid Precursor Protein in Pichia pastoris: Immunodetection of α-, β-, and γ-Secretase Products," Biochemistry, vol. 37, No. 42, 1998, pp. 14958-14965.

Portelius et al., "Identification of novel N-terminal fragments of amyloid precursor protein in cerebrospinal fluid," Experimental Neurology, vol. 223, 2010, pp. 351-358.

Thinakaran et al., "Amyloid Precursor Protein Trafficking, Processing, and Function," The Journal of Biological Chemistry, vol. 283, No. 44, Oct. 31, 2008, pp. 29615-29619.

Wu et al., "Characterization of Plasma β-Secretas(BACE1) Activity and Soluble Amyloid Precursor Proteins as Potential Biomarkers for Alzheimer's Disease," Journal of Neuroscience Research, vol. 90, 2012, pp. 2247-2258.

Yang et al., "Elevated β-secretase expression and enzymatic activity detected in sporadic Alzheimer disease," Nature Medicine, vol. 9, No. 1, Jan. 2003, pp. 3-4.

Zetterberg., "Elevated Cerebrospinal Fluid BACE1 Activity in Incipient Alzheimer Disease," Archives of Neurology, vol. 65, No. 8, Aug. 2008, pp. 1102-1107.

English translation of International Preliminary Report on Patentability and Written Opinion issued Aug. 14, 2014, in PCT International Application No. PCT/JP2013/052317.

| ka, 1/Ms | kd, 1/s | KD |
|---|---|---|
| 3.22E+05 | 1.41E-04 | 4.40E-10 |

| ka, 1/Ms | kd, 1/s | KD |
|---|---|---|
| 9.08E+04 | 5.62E-05 | 6.19E-10 |

Figure 10
(a)
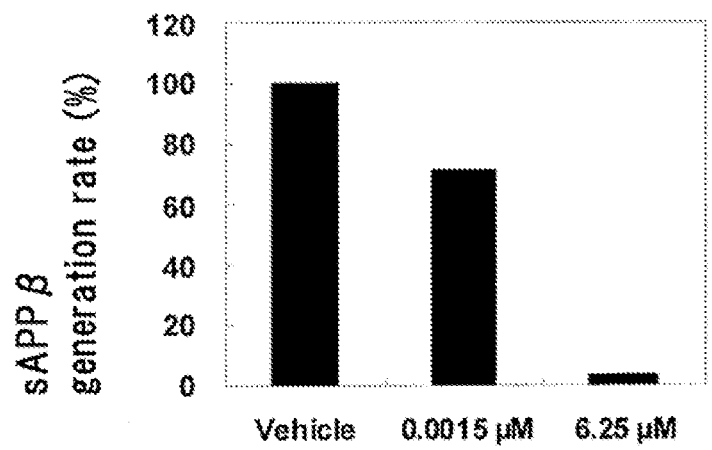
(b)
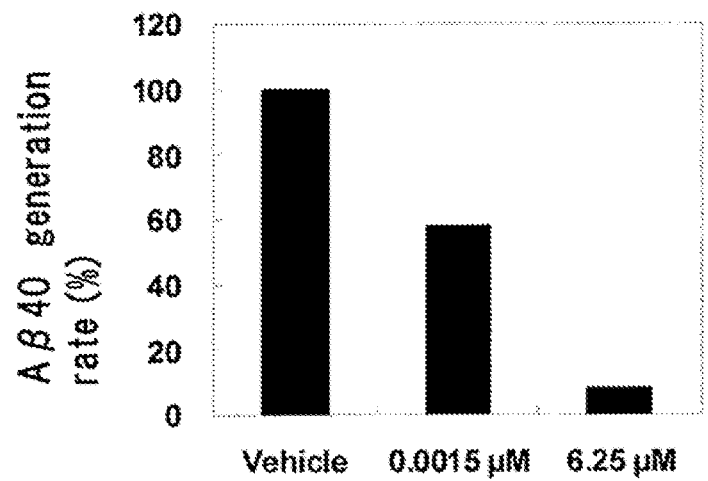

Figure 14

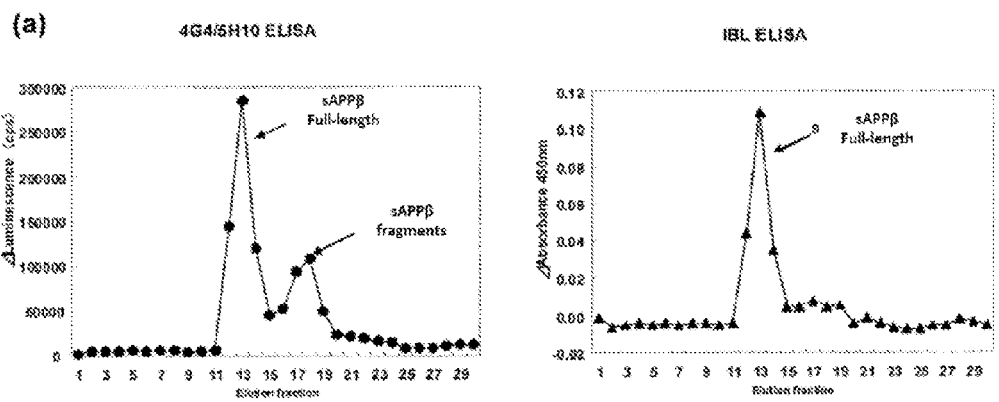

Figure 15

```
4G4-VH:        EMKLVESGGGLVEPGGSLKLSCAASGFTFSNYAMSWVRQTPDKRLEWVASIGRGGSTF
(SEQ ID NO 12) YPDSVKGRFTISRDRVRNILYLQMNSLRSEDTAIYYCRVIYSQSISFDYWGQGTTLTVSS

4G4-VL:        DVVLTQTPLTLSVTIGQPASISCKSRQSLLDSDGKTYLHWLLQRPGQSPKRLIYLVSKLDS
(SEQ ID NO 13) GVPDRFTGSGSGTDFTLKISRVEAEDLGVYYCWQGTHFPFTFGSGTKLEIKRA

5H10-VH:       QVQLQQSGTELAKPGASVKMSCKASGYTFIDYWMHWIKQSPGQGLEWIGFINPRSGST
(SEQ ID NO 14) TYNQKFRDKATLTVDTSSSTAYMQLTSLTSEDSAVYYCTRPDFDYFDYWGQGTTLTVSS

5H10-VL:       DVLMTQTPLSLPVSLGDHASISCRSSQSIVQSNGNTYLEWYLQKPGQSPKLLIYKVSNRF
(SEQ ID NO 15) SGVPDRFSGSGSGTDFTLKISSVEAEDLGIYYCFQASHVPLTFGAGTKLELKRA
```

Figure 17

| Peak | Sequence | SEQ ID |
|---|---|---|
| No.2 | DRGLTTRPGSGLTNIKTEEISEVKM | 28 |
| No.2 | ADRGLTTRPGSGLTNIKTEEISEVKM | 29 |
| No.2 | EVEPVDARPAADRGLTTRPGSGLTNIKTEEISEVKM | 30 |
| No.2 | TENEVEPVDARPAADRGLTTRPGSGLTNIKTEEISEVKM | 31 |
| No.2 | DSVPANTENEVEPVDARPAADRGLTTRPGSGLTNIKTEEISEVKM | 32 |
| No.2 | GADSVPANTENEVEPVDARPAADRGLTTRPGSGLTNIKTEEISEVKM | 33 |
| No.2 | FGADSVPANTENEVEPVDARPAADRGLTTRPGSGLTNIKTEEISEVKM | 34 |
| No.2 | SFGADSVPANTENEVEPVDARPAADRGLTTRPGSGLTNIKTEEISEVKM | 35 |
| No.3 | LDDLQPWHSFGADSVPANTENEVEPVDARPAADRGLTTRPGSGLTNIKTEEISEVKM | 36 |

Figure 18

| The comparison of sAPP$\beta$ ELISA | |
|---|---|
| The number of CSF of AD patients | 5 |
| Age (years) | 74.4 ± 11.3 |
| MMSE score | 17.8 ± 2.6 |
| full-length sAPP$\beta$ by MSD kit (pmol/L) | 773.5 ± 366.3 |
| total (full-length/fragment) sAPP$\beta$ by shionogi kit (pmol/L) | 5193.3 ± 2179.9 |
| Fulll-length sAPP$\beta$ content rate (%, MSD/shionogi) | 14.5 ± 2.0 |
| Detection improvement ratio (fold, shionogi/MSD) | 7.0 ± 1.1 |

ANTI-SAPPβ ANTIBODY

SEQUENCE LISTING

The text file titled Seq_List_07292015.txt of size 15 KB created Jul. 29, 2015, filed herewith, is hereby incorporated by reference.

TECHNICAL FIELD

The present invention concerns an antibody for quantification of sAPP β and methods by using those.

BACKGROUND ART

Alzheimer's disease (also described as AD hereafter) is one of the most typical neurodegenerative diseases involving the old ages. Progressive memory defect or decline in spatial or linguistic cognitive function is main feature of this disease. It is understood that main cause of the decline in these cognitive function is amyloid beta peptides (also described as Aβ hereafter) accumulate on cerebral parenchyma and then formed amyloid plaque causes degeneration of nerve cells (Non-patent document 2 and 3).

The accumulation of Aβ, consisting of especially 39-43 base length of amino acid, is considered the cause of AD (Non-patent document 1). Aβ is generated from amyloid precursor protein (also described as APP hereafter) by being cleaved with two kind of proteases, (β-secretase (also described as BACE1 hereafter) and γ-secretase, which are β-amyloid protease.

It is recently reported that the activity of BACE1 rises in the brain of AD patient and cerebral fluid (Non-patent document 4 and 5). This indicates that BACE1 is promising target for anti-AD medicine and is potential marker for AD.

In addition, generation of soluble APPβ (soluble Amyloid Precursor Protein also described as sAPP β (hereafter) relates to BACE1 activity and therefore has been used as indicator for screening for anti-AD medicine. Furthermore, it is reported that sAPP β is useful for marker for Alzheimer's disease (Non-patent document 6). Therefore, a method for quantifying sAPP β with accuracy and a high sensitivity is desired.

PRIOR ART DOCUMENTS

Non-Patent Documents

Non-Patent Document 1: The Journal of Biological Chemistry, Vol. 283, p. 29615 (2008)
Non-Patent Document 2: Preventing Chronic Disease, Vol. 3, A34 (2006)
Non-Patent Document 3: Brain Pathology, Vol. 1, p. 213 (1991)
Non-Patent Document 4: Nature Medicine, Vol. 9, p. 3 (2003)
Non-Patent Document 5: Archives of Neurology, Vol. 65, p. 1102 (2008)
Non-Patent Document 6: Journal of Neuroscience Research, Vol. 90, p. 2247 (2012)

SUMMARY OF THE INVENTION

Problem to be Solved by the Invention

An object of the present invention is to provide means for quantifying sAPP β with accuracy and a high sensitivity.

Means for Solving the Problems

The preset inventors initially found the fact that sAPP β exist abundantly as a fragment form as well as a full-length form in samples such as serum or cerebrospinal fluid. The present invention is based on the findings and the objective is achieved by the present invention.

Thus, the present invention relates to:

[1] A monoclonal antibody or a part thereof, recognizing C-terminal fragments of sAPP β;
[2] The monoclonal antibody or a part thereof described in [1], wherein said C-terminal fragment of sAPP β is any one of amino acid sequence of SEQ ID NO: 28 to 36;
[3] A monoclonal antibody against sAPP β or a part thereof, recognizing a region described as SEQ ID NO: 28 within amyloid precursor protein;
[4] A monoclonal antibody against sAPP β or a part thereof, recognizing a region described as SEQ ID NO: 37 within amyloid precursor protein;
[5] A monoclonal antibody against sAPP β or a part thereof, having
1) a heavy chain variable region having the amino acid sequence of SEQ ID NO: 14, or in the amino acid sequence of SEQ ID NO: 14, a heavy chain variable region including those having substitution, addition or deletion of one or several amino acid and
2) a light chain variable region having the amino acid sequence of SEQ ID NO: 15, or in the amino acid sequence of SEQ ID NO: 15, a light chain variable region including those having substitution, addition or deletion of one or several amino acid;
[6] A monoclonal antibody against sAPP β or a part thereof, having
1) a heavy chain variable region having the amino acid sequence of SEQ ID NO: 14 and
2) a light chain variable region having the amino acid sequence of SEQ ID NO: 15;
[7] A monoclonal antibody against sAPP β or a part thereof, having
   1) a heavy chain variable region including the following amino acid sequence: DYWMH (SEQ ID NO: 22) FIN-PRSGSTTYNQKFRD (SEQ ID NO: 23) and PDFDY-FDY (SEQ ID NO: 24) or in at least one CDR of the three CDR set, a heavy chain variable region including those having substitution, addition or deletion of one or several amino acid and
   2) a light chain variable region including the following amino acid sequence: RSSQSIVQSNGNTYLE (SEQ ID NO: 25) KVSNRFS (SEQ ID NO: 26) FQASHVPLT (SEQ ID NO: 27) or in at least one CDR of the three CDR set, a light chain variable region including those having substitution, addition or deletion of one or several amino acid;
[8] A method for quantifying sAPP β using the monoclonal antibody or a part thereof described in any one of [1]-[7];
[9] The method described in [8], using a combination with a monoclonal antibody recognizing specifically neoepitope of sAPP β or a part thereof;
[10] A method of selecting a biological sample from a patient of diseases related to sAPP β, comprising a step of quantifying sAPP β in the biological sample by using the monoclonal antibody or a part thereof described in any one of [1]-[7];
[11] The method described in [10], using a combination with a monoclonal antibody recognizing specifically neoepitope of sAPP β or a part thereof;
[12] A method for screening for an inhibitor of BACE1, which is indexed by the amount of sAPP β, using the monoclonal antibody or a part thereof described in any one of [1]-[7];
[13] The method of described in [12], using a combination with a monoclonal antibody recognizing specifically neoepitope of sAPP β or a part thereof;

[14] A kit including the monoclonal antibody or a part thereof described in any one of [1]-[7];

[15] A method for diagnosing diseases related to sAPP β, using the monoclonal antibody or a part thereof described in any one of [1]-[7];

[16] A monoclonal antibody against sAPP (or a part thereof, having
1) a heavy chain variable region having the amino acid sequence of SEQ ID NO: 12, or in the amino acid sequence of SEQ ID NO: 12, a heavy chain variable region including those having substitution, addition or deletion of one or several amino acid and
2) a light chain variable region having the amino acid sequence of SEQ ID NO: 13, or in the amino acid sequence of SEQ ID NO: 13, a light chain variable region including those having substitution, addition or deletion of one or several amino acid;

[17] A monoclonal antibody against sAPP (or a part thereof, having
1) a heavy chain variable region including the following amino acid sequence: NYAMS (SEQ ID NO: 16) SIGRGGSTFYPDSVKG (SEQ ID NO: 17) and IYSQSISFDY(SEQ ID NO: 18)
or in at least one CDR of the three CDR set, a heavy chain variable region including those having substitution, addition or deletion of one or several amino acid and
2) a light chain variable region including the following amino acid sequence: KSRQSLLDSDGKTYLH (SEQ ID NO: 19) LVSKLDS (SEQ ID NO: 20) WQGTHFPFT (SEQ ID NO: 21) or in at least one CDR of the three CDR set, a light chain variable region including those having substitution, addition or deletion of one or several amino acid;

[18] A C-terminal fragment of sAPP 3;
[19] A C-terminal fragment of sAPP β described as any one of amino acid sequence of SEQ ID NO: 28 to 36;

Effect of the Invention

A monoclonal antibody of the present invention or a part thereof, is useful for quantifying sAPP β in a biological sample accurately because that can detect fragments of sAPP β in body as well as a full-length of the same. Accordingly, the monoclonal antibody of the present invention or a part thereof, is also useful for a screening assay for BACE1 inhibitors and a diagnosis for diseased related to sAPP β.

BRIEF DESCRIPTION OF THE DRAWINGS

FIG. 10 shows the results of inhibitory activity of sAPP β(a) and Aβ(b) production in cells, which were measured by the sandwich ELISA of the 4G4/5H10.

FIG. 14 shows the results of sAPP β in plasma (a) and cerebrospinal fluid (b), achieved by separation with molecular weight through a gel filtration.

FIG. 15 shows the amino acid sequences of the variable regions of 4G4 and 5H10. The underlined sequences in each sequence indicate the complementarity-determining regions.

FIG. 17 shows amino acid sequences of sAPP β fragments, of which structures were determined by LC-ESI-MS/MS analysis.

FIG. 18 shows the comparison data of the measured value of sAPP β ELISA with third parties kit, employing CSF from patients of Alzheimer's disease.

DETAILED DESCRIPTION OF THE PREFERRED EMBODIMENT

Definitions

Figures 1, 2:
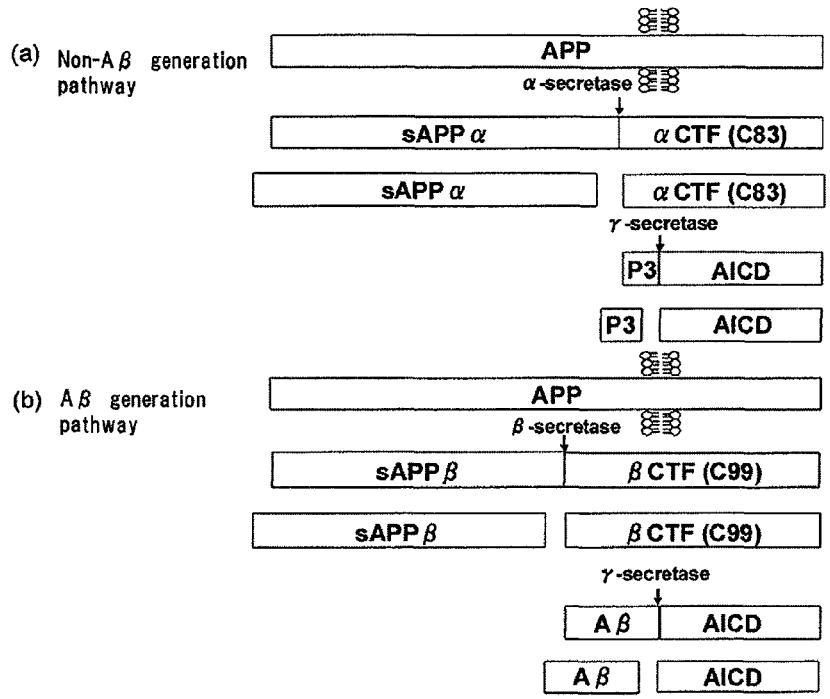
FIG. 1 shows catabolic pathway of amyloid precursor protein (APP).
FIG. 2 shows partial sequences of amyloid precursor protein (APP) (SEQ ID NO: 38) in several animals, and antigen sequences used to prepare the antibodies Immunogen 1 (SEQ ID NO: 2) shows antigen sequence for anti-neoepitope antibody 4G4, and Immunogen 2 (SEQ ID NO: 6) shows antigen sequence for anti-internal structure antibody 5H10.

Unless defined otherwise, all technical and scientific terms used herein have the same meaning as commonly understood by one of ordinary skill in the art to which this invention pertains.

As used herein, "β secretase 1 (BACE1)" refers to an enzyme, which cleave Amyloid Precursor Protein (APP) at β site. For example, BACE1 cleaves a site described as β site in Amyloid Precursor Protein. Its amino acid sequence is already known and is disclosed (Genbank Accession No: AAH36084).

It is known that Amyloid Precursor Protein (APP) has several variants, and respectively described as APP695, APP751 and APP770. "Amyloid Precursor Protein" and "APP" as used herein includes all these variant. Of two fragments, which are generated from APP by the cleavage with APP, a fragment comprising N-terminal site of APP is described as sAPP β. Additionally, C-terminal region, generated newly in being cleaved with BACE1, is described as "neoepitope". When Amyloid Precursor Protein is APP770 (Genbank Accession No: P05067), the sAPP β corresponds to the 18-671 region. Furthermore, it is recently reported that in patients of Alzheimer's disease or Mild Cognitive Impairment (MCI), the concentration of sAPP β increased in blood (Journal of Neuroscience Research, Vol. 90, p. 2247 [2012]).

The present inventors initially discovered the fact that sAPP β in sample such as plasma and cerebrospinal fluid exists abundantly as fragments as well as a full-length. More specifically, it is found that after cleaved by BACE1, further deleted of N-terminal site of sAPP β by something, a fragment maintaining C-terminal site (also refer to C-terminal fragment of sAPP (hereafter) is generated. Also, as used herein, "sAPP β" refers to a full-length sAPP β, occasionally including the C-terminal fragments of sAPP β.

It is reported that N-terminal region of APP (101-108) exists in cerebrospinal fluid (Exp Neurol. 2010 June; 223(2): 351-8) and that peptides consisting of a part of APP (25 base) and a part of APP β exist (Neurodegener Dis. 2009; 6(3):87-94). However, these fragments are not related to the C-terminal fragments of sAPP β and do not indicate the BACE1 activity.

It is recently reported that N-terminal fragment of APP in body are likely generated by the action of meprin β, one of metalloprotease (J Bio Chem. 2011 Aug. 5; 286(31):27741-50). However, this fact does not indicate the existence of the C-terminal fragments of sAPP β.

So far, a monoclonal antibody for quantifying sAPP β, generated by α-secretase, is reported. Monoclonal antibodies as described in US Publication 2003/0166019 and Japan Publication H09-178743) recognize a part of Aβ.

Quantification of sAPP β is performed by an antibody recognizing neoepitope region, which is the terminal structure generated by the cleavage of BACE1, in combination with an antibody recognizing N-terminal region of a full-length sAPP β (WO2008/008643, Journal of Neuroscience Research, Vol. 90, p. 2247 [2012] and the same Vol. 89, p. 822, [2011]).

ELISA kit for quantification of sAPP β is now sold from Covance, IBL and Meso Scale Discovery (MSD). The kit of Covance and MSD includes an antibody recognizing N-terminal region of a full-length sAPP β (see PLoS One, Vol. 6, e23600 [2011]). Furthermore, in the kit of IBL, the antibody recognizing N-terminal region of a full-length sAPP β is used, which is discovered by the present inventors (see Examples).

By these known antibodies, quantifying C-terminal fragments of sAPP β, which exist abundantly in plasma or cerebrospinal fluid, is impossible. Therefore, it is likely that the amount of sAPP β is misestimated as an index of BACE1 activity because of the effect of the secondary protease digestion after the cleavage with BACE1.

The monoclonal antibody of the present invention is a monoclonal antibody characterized in specifically recognizing the C-terminal fragments of sAPP β. Herein, "C-terminal fragments of sAPP β" refers to generic term of fragments in C-terminal side, among fragments, which is further generated by the action of the peptidase or the like, from a full-length sAPP β generated by BACE1. Example of such fragments is peptide having the amino acid sequence of SEQ ID N0.28 to 36.

Furthermore, the monoclonal antibody of the present invention includes a monoclonal antibody recognizing a region described as SEQ ID N0.28 in an amyloid precursor protein, or a part thereof. This region corresponds to position 647-671 when the amyloid precursor protein is APP770, position 572-596 when is APP695 and position 628-652 when is APP751. This antibody is capable of capturing either a full-length sAPP β or C-terminal fragment of sAPP β having the amino acid sequence of SEQ ID N0.28 to 36 and so is useful for quantifying the amount of sAPP β accurately.

The monoclonal antibody of the present invention includes a monoclonal antibody recognizing a region described as SEQ ID N0.37 in amyloid precursor protein, or a part thereof. This region corresponds to position 647-662 when the amyloid precursor protein is APP770, position 572-587 when is APP695 and position 628-643 when is APP751. This antibody is capable of performing a sandwich assay such as ELISA in combination with a monoclonal antibody (for example, 4G4 shown in Example 4) recognizing a neoepitope region described as SEQ ID NO. 1 (corresponds to position 663-671 in APP770).

An example of the monoclonal antibody of the present invention is 5H10 as shown in Examples. This monoclonal antibody recognizes some region within an amino acid sequence described as SEQ ID NO: 37 (position 651-660 of APP770: SEQ ID NO: 11).

As a result of determination of amino acid sequences of variable regions of 5H10 (FIG. 15), a heavy chain variable region has an amino acid sequence described as SEQ ID NO: 14 and a light chain variable region has an amino acid sequence described as SEQ ID NO: 15. In addition, CDRs (complementarity determining region) were determined. Consequently, in an immunoglobulin heavy variable region (VH), CDR1 was DYWMH (SEQ ID NO: 22), CDR2 was FINPRSGSTTYNQKFRD (SEQ ID NO: 23) and CDR3 was PDFDYFDY (SEQ ID NO: 24). Also, in an immunoglobulin light variable region (VL), CDR1 was RSSQSIVQSNGN-TYLE (SEQ ID NO: 25), CDR2 was KVSNRFS (SEQ ID NO: 26) and CDR3 was FQASHVPLT (SEQ ID NO: 27).

The monoclonal antibody of the present invention includes monoclonal antibodies, substantially identical to 5H10. Specifically, variants, having substitution, addition or deletion of one or several amino acid in a heavy chain variable region (SEQ ID NO: 14) and a light chain variable region (SEQ ID NO: 15), are included, as far as maintaining a required bioactivity of the present invention (for example: recognize the region shown as SEQ ID NO: 28 within amyloid precursor protein). Similarly, variants, having substitution, addition or deletion of one or several amino acid in CDR (complementarity determining region), are included, as far as maintaining a required bioactivity of the present invention (for example: recognize the region shown as SEQ ID NO: 28 within amyloid precursor protein).

The immunogen used for generation of the monoclonal antibody of the present invention may be prepared using a method as described, for example, in *Antibodies: A Laboratory Manual* (1989, Cold Spring Harbor Laboratory Press).

Immunization may be performed using a conventional method, for example, by administering the immunogen to mammals by injection, such as intravenous, intradermal, subcutaneous, or intraperitoneal injection. More specifically, for example, the immunogen is diluted to a suitable concentration with, for example, physiological saline-containing phosphate buffer (PBS) or a physiological saline solution, and administered to test animals several times at intervals of 2-3 weeks in combination, if desired, with a conventional adjuvant. When mice are used, the dose per administration is approximately 50-100 µg for each mouse. As used herein, the adjuvant refers to a substance that enhances the immune response in a non-specific manner when administered in combination with the antigen. Conventionally used adjuvants include, for example, pertussis vaccines and Freund's adjuvant. An antiserum may be obtained by drawing blood from a mammalian animal 3-10 days after the final immunization.

A method for produce a monoclonal antibody may be carried out by preparing fusion cells (hybridomas) between plasma cells from mammals immunized with the immunogen (immune cells) and mammalian plasmacytoma cells (myeloma cells), selecting, from these hybridomas, a clone that produces a desired monoclonal antibody that recognizes sAPPβ, and then culturing the clone. Basically, the production of the monoclonal antibody may be conducted in accordance a conventional method.

In the method, the mammals to be immunized with the immunogen are desirably selected in consideration of the compatibility with the plasmacytoma cells used for cell fusion; mice, rats and the like are used. The immunization method is the same as that used for preparation of polyclonal antibodies. However, spleen cells are removed from the immunized animals 3-10 days after the final immunization.

To obtain hybridomas from the immune cells thus obtained, a method described in "Experimental Manual for Molecular Cell Biology" (Takekazu Horie et al., published in 1994, Nankodo) may be used. In order to form cells that can be passaged by subculture, plasmacytoma cells are fused with the antibody-producing immune cells; for example, in the presence of sendaivirus or polyethylene glycol, whereby hybridomas may be obtained. The plasmacytoma cells used here are desirably plasmacytoma cells derived from a homothermal animal of the same species; for example, when fused with spleen cells obtained using mice as immunized animals, mouse myeloma cells are preferably used. Known cells, such as p3×63-Ag8.UI, may be used as the plasmacytoma cells.

Hybridomas are selected with HAT medium (supplemented with hypoxanthine, aminopterin, and thymidine). Once emergence of colonies is observed, the antibodies secreted into the culture supernatant are tested (screened) for the binding to the antigen, whereby a hybridoma that produces an antibody of interest may be obtained.

The screening methods include various methods generally used for detection of antibodies, for example, the spot test, the agglutination reaction test, Western-blotting, and ELISA. Preferably, as detailed below, the screening method is carried out according to the ELISA method on the hybridoma culture supernatant, using the reactivity with the upstream region of C-terminal neoepitope structure as an indicator. By this screening, it is possible to screen for an isolate that produces an antibody of interest that is specifically reactive with the upstream region of C-terminal neoepitope structure. Clone 5H10 is an example of the clones obtained based on this process.

Cloning of the isolates obtained as a result of the screening which are capable of producing antibodies of interest may be carried out by a conventional method, such as limiting dilution analysis or soft agar analysis. The cloned hybridomas may be cultured in a large scale, if necessary, either in serum-containing or serum-free medium. By this culture, it is possible to obtain the desired antibody with a relatively high purity. Alternatively, it is possible to inoculate the hybridomas into the abdominal cavity of mammals, such as mice, that are compatible with the hybridomas to recover the desired antibody in large quantity as mouse ascites fluid.

The culture supernatant and mouse ascites fluid that contain the hybridoma that produces the monoclonal antibody of the present invention may be used as a crude antibody solution without purification or modification. Isolation/purification of the monoclonal antibody may be carried out by subjecting the culture supernatant or the ascites fluid to saturated ammonium sulfate, ion exchange chromatography (e.g., DEAE or DE52), or affinity column chromatography, such as anti-immunoglobulin column or protein A column chromatography.

Alternatively, a recombinant antibody produced using a genetic recombination technique by cloning an antibody gene, inserting it into an appropriate vector, and introducing the vector into a host may be used as the monoclonal antibody of the present invention (for example, Carl et al., THERAPEUTIC MONOCLONAL ANTIBODIES, published in 1990).

Specifically, cDNA encoding the variable regions (for example, SEQ ID NO: 14 and 15 from 5H10) of the objective antibody (for example, 5H10) are synthesized. For synthesis and amplification of the cDNA, 5'-Ampli FINDER RACE Kit (Clontech) and the 5'-RACE method using PCR (Frohman, M. A. et al, Proc. Natl. Acad. Sci. USA, Vol. 85, p. 8998 [1988]) may be available. DNA fragments of interest are purified from the obtained PCR product and ligated to vector DNA. Further, desired recombinant vectors are prepared by introducing recombinant vectors into a host such as E. coli, and selecting colonies. The nucleotide sequences of the objective DNA are confirmed by a known method, such as the dideoxy method.

Once the DNAs encoding the V region of the objective antibody have been obtained, they are ligated to DNA encoding the desired antibody constant region (C region) and integrated into expression vector. Alternatively, the DNAs encoding the V region of the antibody may be integrated into expression vector containing DNA encoding the antibody C region. To prepare the antibody for use in the present invention, the antibody gene is integrated into an expression vector so as to be expressed under the control of an expression regulatory region, for example, under the control of an enhancer/promoter. Then, host cells may be transformed with this expression vector to express the antibody.

Expression of the antibody gene can be achieved either by cotransformation of a host with expression vectors into which the heavy chain (H chain) and light chain (L chain) of the antibody are separately integrated, or by transformation of a host with a single expression vector into which DNA encoding both the H and L chains is integrated (see WO94/11523)

Upon performing immunoassay as described below, the antibody by itself may usually be labeled with various agents to allow its activity to be detected. Preferred embodiments of the monoclonal antibody of the present invention include a labeled monoclonal antibody. An antibody can be labeled by conventional methods such as described in "Experimental Manual for Molecular Cell Biology" (Takeichi Horie et al., 1994, Nankodo). Examples of the various agents include a chemiluminescent substance, an enzyme, a fluorescent substance, colored beads, a radioisotope, an element, a metal, biotin and the like. Specific examples include the following, but are not limited thereto. The chemiluminescent substance refers to, for example, luminol and acridinium ester. The enzyme refers to, for example, (3-galactosidase, alkaline phosphatase and peroxidase. The fluorescent substance refers to, for example, europium cryptate, FITC (fluorescein isothiocyanate) and RITC (tetramethylrhodamine isothiocyanate). STDC0415 The colored beads refer to, for example, protein A beads, wheat germ agglutinin (WGA) beads and streptavidin beads. The radioisotope refers to, for example, 14C, 125I and 3H. The element refers to, for example, a lanthanide element such as europium. The metal refers to, for example, ferritin and colloidal gold.

As used herein, "a part of monoclonal antibody" refers to a region that is a part of the aforementioned monoclonal antibody of the present invention and has specific binding ability to sAPPβ likewise the monoclonal antibody.

Concretely, Fab (fragment of antigen binding), F(ab')$_2$, Fab', single chain antibody (single chain Fv; hereinafter denoted by scFv), disulfide stabilized antibody (disulfide stabilized Fv; hereinafter denoted by dsFv), dimerized V region fragment (hereinafter, denoted by Diabody), peptide containing CDR, having specific bindability to the human PcrV, can be recited (Expert opinion on therapeutic patents, vol. 6, No. 5, p. 441-456, 1996).

Another embodiment of the present invention is a method for measuring sAPP β which is performed with the monoclonal antibody of the present invention or a part thereof (hereafter also described as a monoclonal antibody or the like of the present invention). A monoclonal antibody or the like are especially useful for immunoassay (immunological assay). The assay method using a monoclonal antibody of the present invention may be a competitive measurement or non-competitive measurement, and may be a homogeneous assay (measurement in homogeneous system) or a heterogeneous assay (measurement in heterogeneous system). Specifically, the assay may be conducted according to the conventional methods such as enzyme immunoassay (EIA), enzyme linked immunosorbent assay (ELISA), fluoroimmunoassay (FIA), radioimmunoassay (RIA), time-resolved fluoroimmunoassay (TR-FIA), chemiluminescent immunoassay, immunoblotting, western blotting, immunostaining, SPA, fluorescence polarization assay (FP), and fluorescence resonance energy transfer (FRET).

A preferable embodiment includes enzyme linked immunosorbent assay (ELISA). ELISA is a method utilizing an antibody or antigen labeled with an enzyme to quantify an amount of antibody or antigen by an activity of a label-enzyme. To separate an antigen-antibody binding reactant from a labeled antigen and an antibody in free form, immobilized antibody and antigen are used. For immobilization, agarose, the inside of a microtiter plate, latex particle and the like may be used. Specific examples of ELISA include a competitive immunoassay, a double antibody sandwich immunoassay and the like. Examples of the labeled enzyme include a horseradish peroxidase (hereinafter also described as HRP), alkaline phosphatase and the like.

In an immunoassay such as ELISA, two antibodies are generally used in combination. As another antibody, which are used in combination with the monoclonal antibody of the present invention, an antibody (for example, 4G4), which recognizes specially the C-terminal neoepitope structure of sAPP β (for example, position 588 to 596 in APP695, described as SEQ ID NO:1), is preferable.

The present inventors made it possible to evaluate the C-terminal fragments of sAPPβ, which was not detected by the conventional ELISA kit (see Example 10), by the ELISA, wherein the above antibody which recognizes specially the C-terminal fragments of sAPP β (for example, 5H10) is used in combination with the antibody which recognizes specially the C-terminal neoepitope structure of sAPP β (for example, 4G4). This fact indicates that the amount of sAPP β contained in a biological fluid is reflected accurately, because the method using the antibody of the present invention allows for detecting not only a full-length sAPP β, but also its decomposition product.

On the other hand, in the existing kit for quantifying sAPP β, an epitope of the used antibody is located near N-terminal of sAPP β and thereby the C-terminal fragments of sAPP β lacking of N-terminal region. It cannot be said that the accurate quantification of the amount of sAPP β and the BACE1 activity determination have been carried out, because only some sAPP β can be detected.

The method of the present invention allows for quantifying the C-terminal fragments of sAPP β, so the BACE1 activity can be determined accurately, compared to an existing kit for quantifying sAPP β or an existing antibody for qualifying. Therefore, the method of the present invention is useful for a screening method for a BACE1 inhibitor, selecting a biological sample from patients of diseases to which BACE1 is related, such as Alzheimer's disease, and diagnosing diseases to which BACE1 is related, such as Alzheimer's disease.

One embodiment of the method for quantifying of the present invention is a screening method for BACE1 inhibitors. In this method, after BACE1(enzyme) and APP(substrate) are placed in contact with a test substance, the amount of sAPP β is evaluated and when the value is low as compared to that in the absence of the test substance, the test substance is determined as a BACE1 inhibitor.

Furthermore, cells expressing BACE1 and APP are placed in contact with a test substance and when the amount of sAPP β in an extract or supernatant from cells is low in the presence of the test substance as compared to that in the absence of the test substance, the test substance can be determined as a BACE1 inhibitor.

One embodiment of the method for quantifying of the present invention is application for a trial test or a diagnostic for human.

For example, after a test substance is administered to a patient involved in Alzheimer's disease, a biological sample is collected from a test subject and the amount of sAPP β is evaluated. In this case, when the amount of sAPP β in the biological sample from the test subject is decreased, the test substance is indexed as having medicinal effect against Alzheimer's disease.

Furthermore, by collecting a biological sample from a test subject and quantifying the amount of sAPP β, whether the test subject is involving in the disease to which BACE1 is related, such as Alzheimer's disease or mild cognitive impairment (MCI) or not, or the possibility of the future disease can be determined.

As used herein, "biological sample" refers to any biological fluid sample derived from mammal. For example, a body fluid, such as blood, plasma, serum, cerebrospinal fluid (CSF), urine, saliva, and sweat; and an extract or supernatant from cells and/or tissue may be included.

Further another embodiment of the present invention is a kit containing the monoclonal antibody of the present invention or the like. In general, such a kit comprises one or more components necessary to carry out assays. Such components may be reference standards, reagents (diluents and buffers and the like), containers, and/or devices. For example, a container in such a kit may contain a monoclonal antibody capable of binding to a sequence specific for a C-terminal fragment of sAPP β. Such an antibody may be provided in a form attached to any supporting material known to one skilled in the art (for example, wells in a microtiter plate, and a suitable membrane, such as nitrocellulose). Such a kit may further comprises components (for example, reagents or buffers) to be used in assays. Alternatively, such a kit may also be labeled with a substance as described above, which is suitable for direct or indirect detection of antibody binding.

EXAMPLES

The present invention is described below in more detail by way of example. However, the present invention is not limited to the following examples. Also, unless otherwise specified, methods as described in *Immunochemistry in Practice* (Blackwell Scientific Publications) were used as the methods for preparing the antibodies. Also, unless otherwise specified, methods as described in *Molecular Cloning: A Laboratory Manual 2nd Edition* (Cold Spring Harbor Laboratory) were used as the genetic engineering techniques.

Example 1

Generation of the sAPPβ Neoepitope Antibody

Selection of the Immunogen Peptide:
To detect APP cleaved by β-secretase, the antibody of the C-terminal cleavage site was prepared. The sequence of the neoepitope of sAPPβ was shown in FIG. 2. The 9mer neoepitope peptide of sAPPβ, APP695-[588-596] (Thr-Glu-Glu-Ile-Ser-Glu-Val-Lys-Met:SEQ ID NO: 1) was conserved in the animals from human to mice, and used as immunogen.
Immunization:
The N-terminal cysteine-containing neoepitope peptide (Cys-Thr-Glu-Glu-Ile-Ser-Glu-Val-Lys-Met:SEQ ID No.2) was synthesized by SIGMA. 1.3 mg of the peptide was dissolved in 0.5 ml distilled sterile water, and then was mixed to 10 mg of IMJECT® Maleimide Activated mcKLH (Thermo SCIENTIFIC) (kit containing: (i) Activated mcKLH lyophilized in PBS with EDTA, pH 7.2 with proprietary stabilizer; maleimide activation level: >400 moles of maleimide/mole of mcKLH; (ii) Conjugation Buffer, 30 ml, 83 mM sodium phosphate buffer, 0.1 M EDTA, 0.9 M sodium chloride, 0.02% sodium azide, pH 7.2, with stabilizer; (iii) Dextran Desalting Columns (5K MWCO), 5×5 ml, contains 0.02% sodium azide; (iv) and, Purification Buffer Salts, contains 0.083 M sodium phosphate, 0.9 M sodium chloride, pH 7.2 with proprietary stabilizer. The Maleimide Activated mcKLH Kit is for conjugating a sulfhydryl-containing hapten to elicit an immune response and antibody production against a hapten. The mcKLH is pre-activated using a heterobifunctional crosslinker that contains an N-hydroxysuccinimide (NHS) ester and a maleimide group. The activated mcKLH contains a maleimide group that can react with suithydryl-containing peptides.) dissolved in 1 ml distilled sterile water and incubated overnight at 4° C.

The mixture was dialyzed against 0.9% physiological saline, and stored in the freezer at −80° C.

Seven female A/J Jim Slc mice were intraperitoneally immunized at three-week interval with 0.1 mg of the neoepitope peptide-KLH conjugate in emulsion prepared with complete Freund's adjuvant for the first immunization or incomplete Freund's adjuvant for the subsequent immunization. 3-weeks after the final injection, mice were boosted i.v. using 0.1 mg of the KLH-conjugated peptide.
Biotinylation of the Neoepitopeptide:
0.4 mg of the N-terminal cysteine-containing neoepitope peptide was dissolved in 0.4 ml of 0.1M phosphate buffer (pH6.0) including 5 mM EDTA. The peptide solution was mixed to 0.16 mg of EZ-Link® Maleimide-PEG2-Biotin (Thermo Scientific) and incubated for 2 h at room temperature. The biotinylated peptide was purified by reversed-phase HPLC.
Preparation of Hybridoma:
Three days after the boosting, the euthanized two mice were sacrificed to dissect the spleen. Freshly harvested spleen cells and mouse myeloma cells (p3×6363-Ag8) were fused by adding 50% polyethylene glycol 4000. Hybridomas were selected by HAT (hypoxanthine-aminopterin-thymidine) medium.

Screening of the Neoepitope Antibody:
Ten days later hybridoma cell supernatant was screened as follows. Then 384-well MaxiSorp plates (Nunc) were coated with 0.35 µg of anti-mouse IgG (Jackson Immuno Research) in 35 µl of 50 mM Tris-HCl buffer (pH7.5) and incubated for 16 h at 4° C. Each well was aspirated and washed once with 90 µL of washing solution (0.01% Tween20 in Saline) and blocked with 90 µL of BlockAce (DAINIPPON) for 2 h at room temperature.

After once washing, 15 µl of hybridoma supernatants and 10 µl of buffer A (0.15M NaCl, 0.01% Tween80, 0.5% BSA, 0.05% Proclin150 in 50 mM Tris-HCl, pH7.4) and 10 µl of 0.04 ng the biotynylated peptide and 2 ng streptavidin-HRP in buffer A were added to the plates and incubated overnight at 4° C.

The plates were washed three times and 25 µl of TMB substrate solution (DAKO) was added to each well to initiate the color reaction. The reaction was finally stopped by addition of 25 µl of 0.05NH2SO4, and optical absorbance was measured at wavelength of 450 nm.

Figure 3:
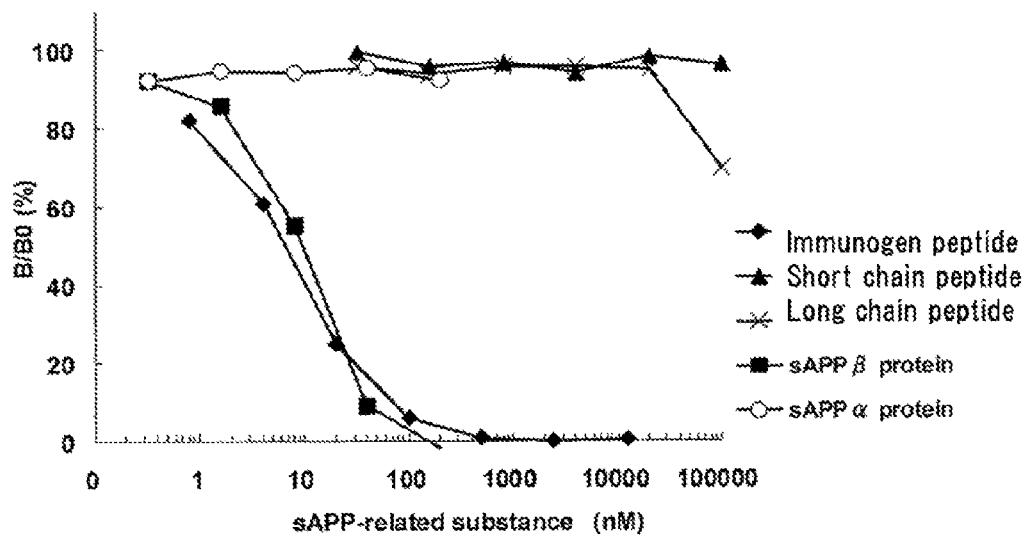
FIG. 3 shows the results of affinity and specificity with anti-neoepitope antibody 4G4, for several APP related substrate (e.g. immunogenic peptides, short-chain peptides, long-chain peptides, sAPP β and sAPP α), which were measured by ELISA.
Figure 4:
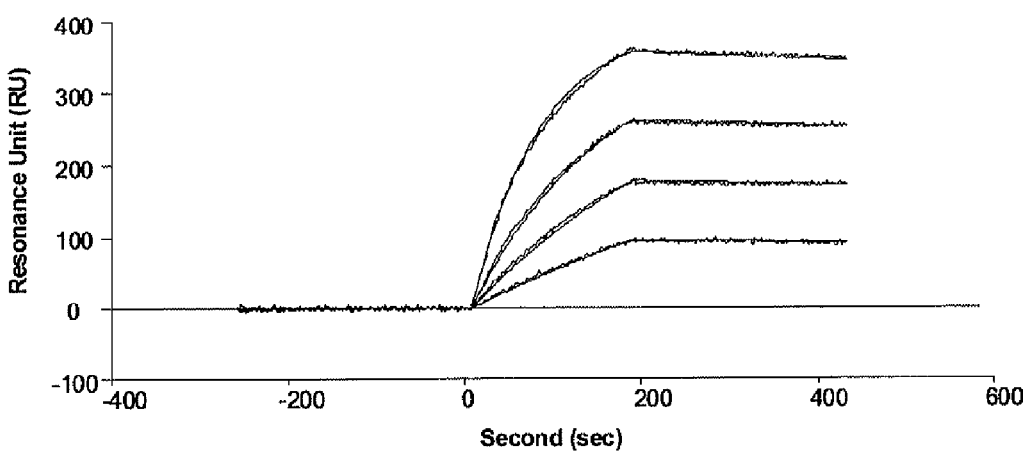
FIG. 4 shows the results of affinity with the anti-neoepitope antibody 4G4 for sAPP β, which was measured by SPR method.

From the result of screening, 4G4 was chosen owing to the highest affinity against the neoepitope peptide. The antibody was determined to be IgG2a/κ by immunoglobulin isotyping ELISA (BD bioscience).
Analysis of the Antibody Affinity by ELISA:
10 µl of the antibody solution containing 4G4 and 10 µl of the immunogen peptide (SEQ ID No.:2) or the long peptide (Thr-Glu-Glu-Ile-Ser-Glu-Val-Lys-Met-Asp: SEQ ID No. 3 SIGMA) or human sAPPβ (MESO SCALE DISCOVERY) or human sAPPα (MESO SCALE DISCOVERY) and 10 µl of 0.04 ng the biotynylated peptide and 2 ng streptavidin-HRP in buffer A were placed into the above anti-mouse IgG-immobilized plates and incubated overnight at 4° C. The plates were washed three times and 25 µl of TMB substrate solution (DAKO) was added and incubated for 30 min. The reaction was finally stopped by addition of 25 µl of 0.05NH2SO4, and optical absorbance was measured at wavelength of 450 nm (FIG. 3). The IC50 of sAPPβ in the competitive ELISA using 4G4 was about 8.4 nM, and cross-reactivity of sAPPα was less than 0.01%.
Affinity of the Antibody, 4G4
Binding affinity of the neoepitope antibody, 4G4 was immobilized on a GLM chip (BIO-RAD) and analyzed using a ProteOn (BIO-RAD). 4 different concentrations of sAPPβ (40, 20, 10, 5 nM) were injected as the analytes. The affinity (KD) was $4.4 \times 10^{-10}$ M (FIG. 4).

Example 2

Generation of the sAPPβ Internal Structural Antibody

Selection of the Immunogen Peptide:
To detect sAPPβ and the fragment, the sequence near the C-terminal neoepitope site was chosen. The sequence was conserved in the animals.

The internal structural sequence of APP was shown in FIG. 1. The 34 mer peptide of sAPPβ, APP695-[552-585: SEQ ID No. 5] was chosen. The C-terminal cysteine-containing peptide (Asp-Ser-Val-Pro-Ala-Asn-Thr-Glu-Asn-Glu-Val-Glu-Pro-Val-Asp-Ala-Arg-Pro-Ala-Ala-Asp-Arg-Gly-Leu-Thr-Thr-Arg-Pro-Gly-Ser-Gly-Leu-Thr-Asn-Cys: SEQ ID No. 6, 35 mer) used as immunogen.
Immunization:
The C-terminal cysteine-containing peptide (SEQ ID No. 6) was synthesized by SIGMA. 4.0 mg of the peptide was dissolved in 0.5 ml distilled sterile water, and then was mixed to 10 mg of Imject® Maleimide Activated mcKLH (Thermo SCIENTIFIC) dissolved in 1 ml distilled sterile water and incubated overnight at 4° C. The mixture was dialyzed against 0.9% physiological saline, and stored in the freezer at −80° C.

Seven female A/J Jim Slc mice were intraperitoneally immunized at three-week interval with 0.1 mg of the neoepitope peptide-KLH conjugate in emulsion prepared with complete Freund's adjuvant for the first immunization or incomplete Freund's adjuvant for the subsequent immunization. 3-weeks after the final injection, mice was boosted i.v. using 0.1 mg of the KLH-conjugated peptide.

Biotinylation of the Internal Structural Peptide:

0.2 mg of the N-terminal cysteine-containing the internal structural peptide was dissolved in 0.2 ml of 0.1M phosphate buffer (pH6.0) including 5 mM EDTA. The peptide solution was mixed to 29 µg of EZ-Link® Maleimide-PEG2-Biotin (Thermo Scientific) and incubated for 2 h at room temperature. The biotinylated peptide was purified by reversed-phase HPLC.

Preparation of Hybridoma:

Hybridoma was prepared by the same method of Example 1.

Screening of the Internal Structural Antibody:

Hybridoma supernatants were screened by the competitive ELISA using biotinylated internal structural peptide (SEQ ID No.: 5) and recombinant human sAPPβ (MESO SCALE DISCOVERY). A few hybridomas were selected on the condition that the antibodies had high affinities.

5H10 was chosen owing to the highest affinity in the acquired antibodies. The antibody was determined to be IgG1/κ by immunoglobulin isotyping ELISA (BD bioscience).

Figure 5:
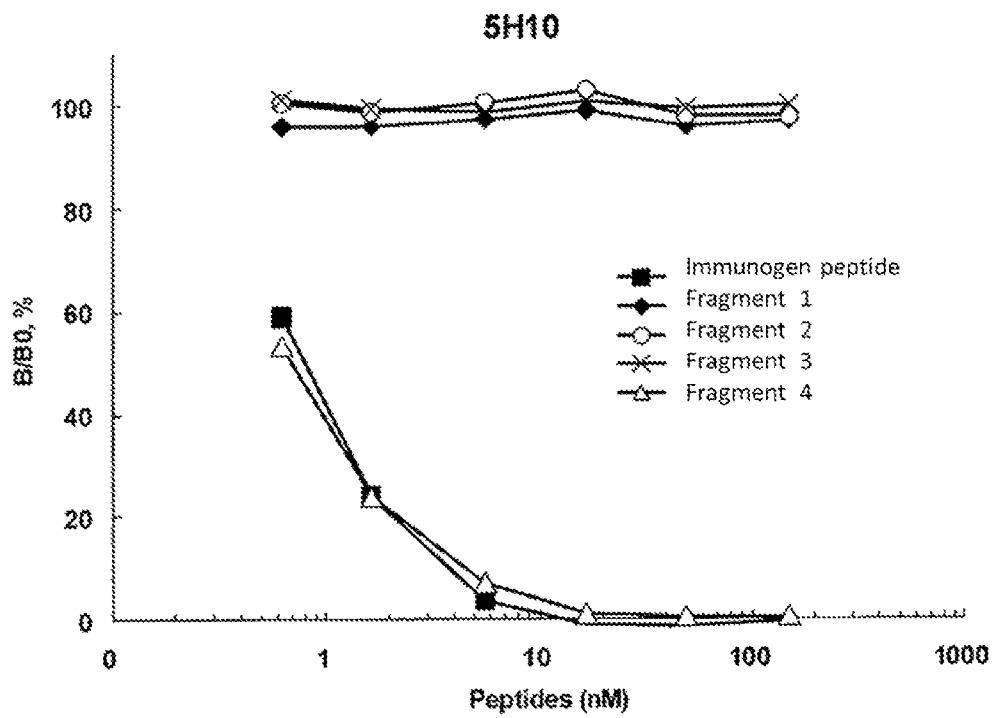
FIG. 5 shows the results of affinity with the anti-internal structure antibody 5H10 for immunogenic peptides and 4 partial peptide thereof, which were measured by ELISA.

Determination of the Antibody Epitope by ELISA:

Reactivity of the antibody, 5H10 to the four fragment peptides 1~4 (SEQ ID No.: 8, 9, 10, 11) was evaluated by competitive ELISA in the same method as Example 1. The result was shown in FIG. 5.

```
Fragment1:
                                     (SEQ ID No.: 8)
Asp-Ser-Val-Pro-Ala-Asn-Thr-Glu-Asn-Glu-Val-Glu Fragment2:
                                     (SEQ ID No.: 9)
Asn-Glu-Val-Glu-Pro-Val-Asp-Ala-Arg-Pro-Ala-Ala Fragment3:
                                    (SEQ ID No.: 10)
Arg-Pro-Ala-Ala-Asp-Arg-Gly-Leu-Thr-Thr-Arg-Pro Fragment4:
                                    (SEQ ID No.: 11)
Thr-Thr-Arg-Pro-Gly-Ser-Gly-Leu-Thr-Asn-Cys
```

Figure 6:
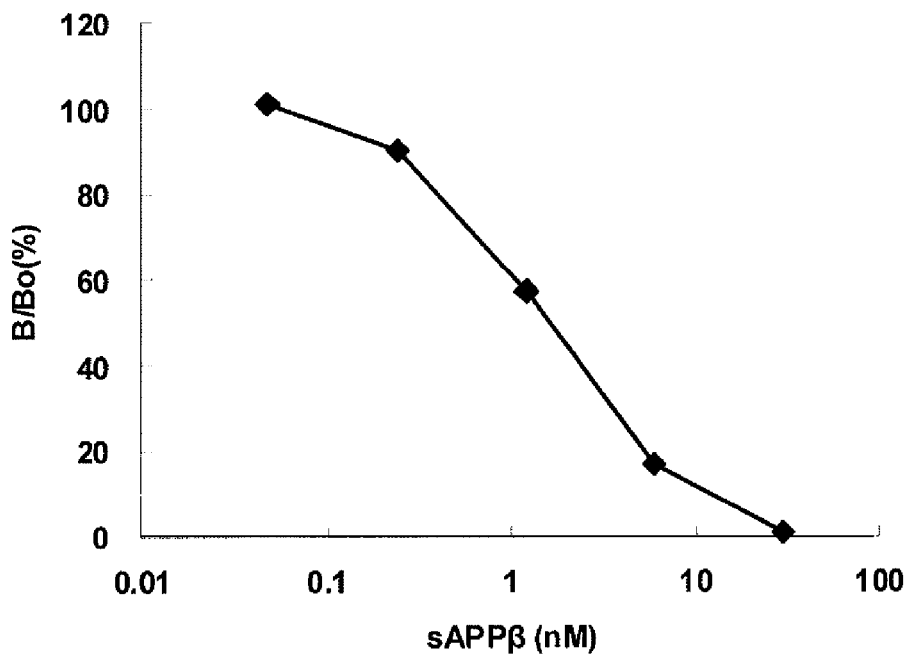
FIG. 6 shows the results of affinity with the anti-internal structure antibody 5H10 for sAPP β, which were measured by ELISA.

Analysis of the Antibody Affinity by ELISA,

IC50 against sAPPβ protein (MESO SCAL DISCOVERY) was calculated by the competitive ELISA as well as Example 1 (FIG. 6).

Affinity of the Antibody, 5H10

Figure 7:
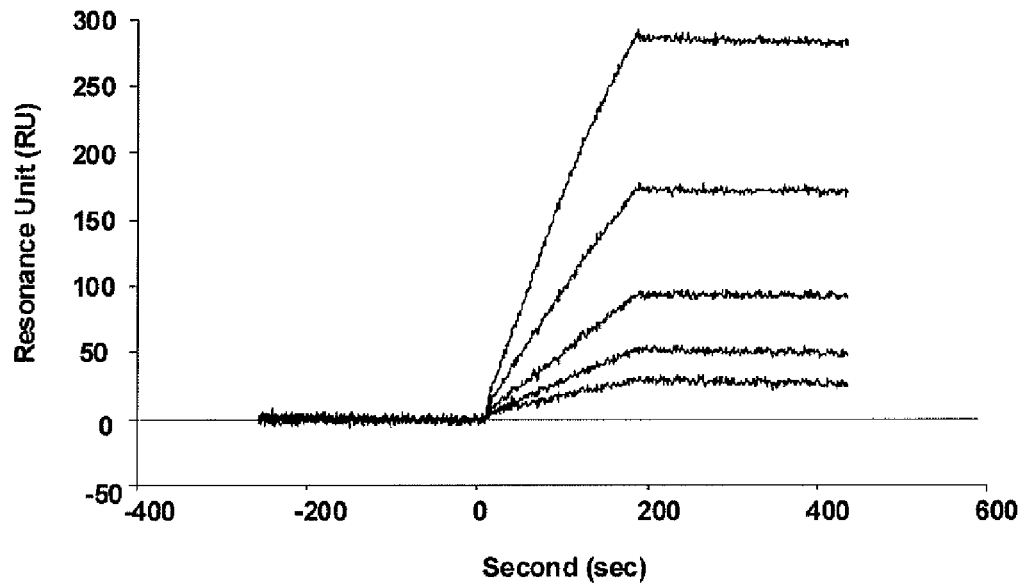
FIG. 7 shows the results of affinity with the anti-internal structure antibody 5H10 for sAPP β, which were measured by SPR.

Binding affinity of the internal antibody, 5H10 was immobilized on a GLM chip (BIO-RAD) and analyzed using a ProteOn (BIO-RAD). 6 different concentrations of sAPPβ (1000, 250, 62.5, 15.6, 3.91 nM) were injected as the analytes. The affinity (KD) was 6.2×10-10 M (FIG. 7).

Example 3

Determination of the Antibody Sequences

The amino acid sequence of VH and VL was determined from hybridomas of 4G4 and 5H10 by the ordinary method. (SEQ ID No.: 12, 13, 14, 15)

Example 4

Construction of 4G4/5H10 Sandwich ELISA

Maxisorp 96-well white plate (Nunc, Cat. No. 437591) was incubated for 16 h at 4° C. with streptavidin (Thermo Scientific, 1 µg/well/100 µL in 50 mM Tris-HCl, pH 7.5). Each well was aspirated and washed once with 300 µL of washing solution (0.01% Tween20 in Saline) and blocked with 300 µL of BlockAce (DAINIPPON) for 2 h at room temperature. After once washing, 200 ng of biotinylated 4G4 IgG labeled with EZ-Link® Maleimide-PEG2-Biotin (Thermo Scientific) was added to each well. The plate was incubated at room temperature for 2 to 4 h. The plate was washed three times, and 100 µL of 0.55-400 µM standard sAPPβ (human sAPP (protein, Meso Scale Discovery) in assay buffer B (0.1M NaCl, 1 mM $MgCl_2$, 0.1 mM $ZnCl_2$, 0.01% Tween80, 0.1% BSA, 10 βg/ml mouse-γ-globulin, 0.05% sodium azide in 50 mM Tris-HCl, pH7.5) or 100 µL of samples which was diluted with assay buffer B were added to each well. The plate was incubated overnight at 4° C. The plate was washed four times, and 100 µL of 5H10 Fab'-ALP (10 ng in assay buffer B) was added to each well. The plate was incubated at room temperature for 2-3 h. The plate was washed four times, and 100 µL of CDP-Star® Emerald II (Applied Biosystems) was added and incubated at room temperature for 15-20 min. The luminescence was measured by plate reader, ARVO (PerkinElmer).

Figure 8:
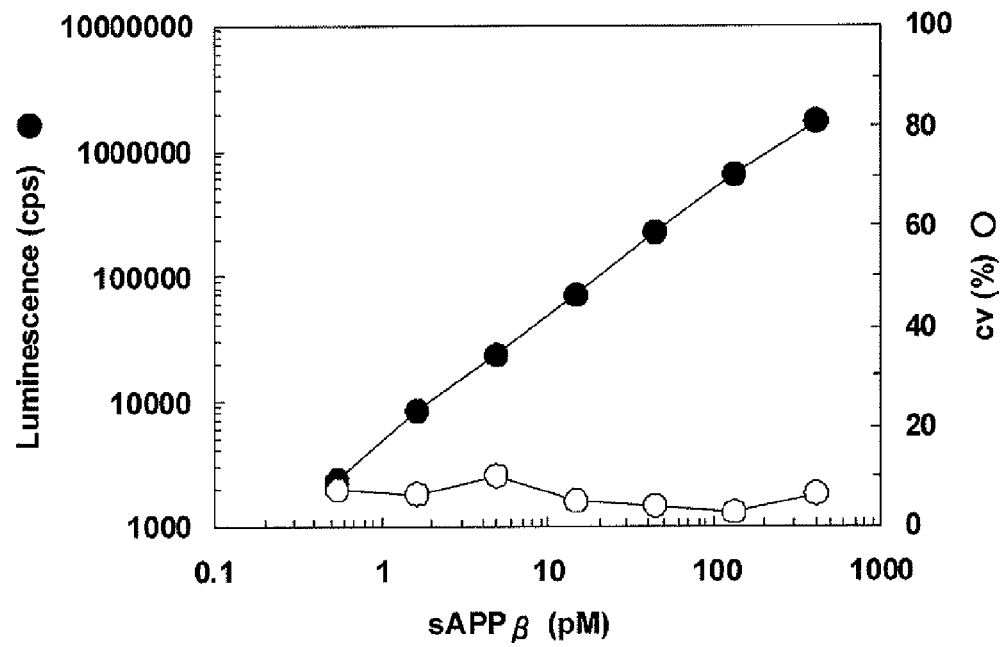
FIG. 8 shows a standard curve of the sandwich ELISA of the 4G4/5H10.
Figure 9:
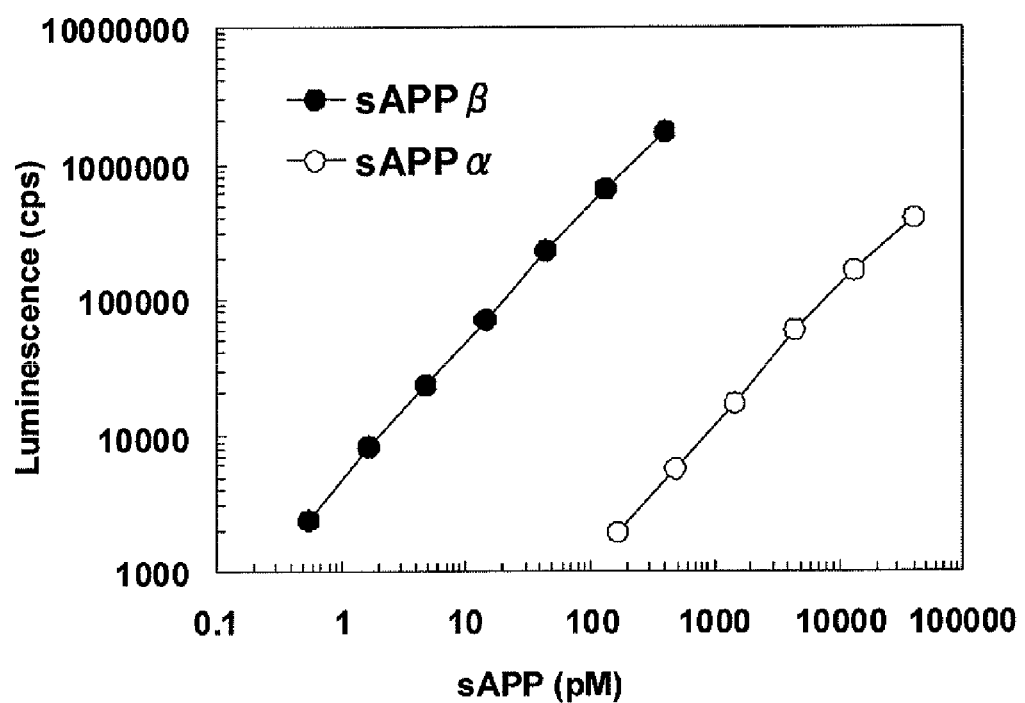
FIG. 9 shows the results of cross reactivity for sAPP α, which were measured by the sandwich ELISA of the 4G4/5H10.

The internal antibody 5H10 IgG was digested to F(ab')2 by incubating with pepsin (Roche). Subsequently, the obtained 5H10 F(ab')2 was reduced to Fab' by incubating with 2-MEA. Sulfo-SMCC (Thermo Scientific) was added to alkaline phosphatase (ALP, highly active, Roche) to introduce maleimide residue. The obtained maleimide-activated ALP was added to 5H10 Fab' to produce 5H10 Fab'-ALP and purified by gel-filtration. The sandwich ELISA had a detection limit of 0.8 µM (FIG. 8). The cross-reactivity with sAPPα was about 0.2% (FIG. 9).

Example 5

Measurement of Inhibition of the Cellular sAPPβ (Full-Length and the C-Terminal Fragments) and Amyloidβ (Aβ) Production Human neuroblastoma SH-SY5Y cells with overexpression of human wild type APP (SH/APPwt) were seeded at 1.2×10⁵ cells per well in a 96-well plate (Falcon) and incubated for 2 h at 37° C. in an atmosphere of 5% $CO_2$. And then, 50 µl of compound A (compound 622 described in WO2008/133273, 4% DMSO) was added and incubated for 24 h. Therefore, final concentration of DMSO was 1% and total volume per well was 200 µl. 100 µl of the cell culture supernatants were collected and measured the concentrations of sAPPβ and Aβ.

sAPPβ levels were measured by above 4G4/5H10 sandwich ELISA. For measurement of Aβ levels, 10 µl of HTRF soln. (Amyloid (1-40 peptide; IBA Molecular Holding, S.A.) and 10 µl of the cell culture supernatants were added to black 384-well plates (Costar) and incubated in the absence of light at 4° C. overnight. Fluorescence intensity was measured (Ex: 665 nm, 620 nm: 320 nm, Em) by Wallac 1420 Multilabel counter (Perkin Elmer Wallac). Aβ levels were calculated from the ratio according to the formula (10000×665 nm/625 nm). The overall results showed that compound A displayed a dose-dependent inhibition of Aβ and sAPPβ production (FIGS. 10a,b).

Example 6

Measurement of sAPPβ in Dog CSF and Plasma after Dosing of BACE1 Inhibitor

Figure 11:
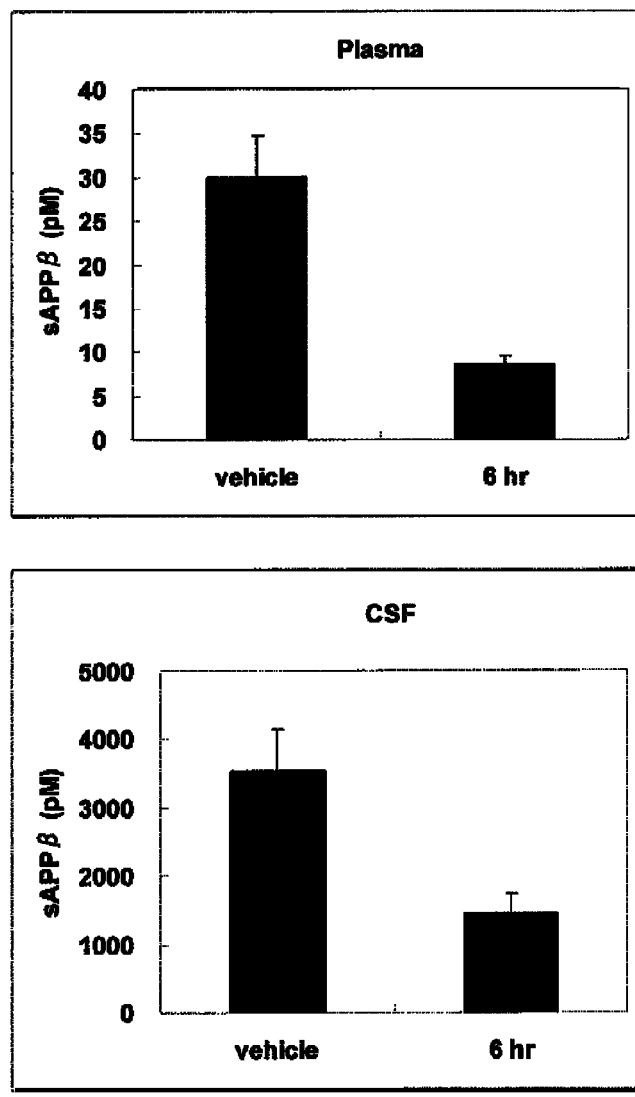
FIG. 11 shows the results of sAPP β in plasma and cerebrospinal fluid of rats to which were administered BACE1 inhibitors, which were measured by the sandwich ELISA of the 4G4/5H10.

Vehicle (0.5 w/v % methyl cellulose) or 30 mg/15 ml/kg of compound A were orally dosed to 27~9-weeks old Crj: SD rats (male, 5 each). CSF and plasma samples were collected from these rats at 6 h after the administration. CSF samples were collected from the cisterna magna of anesthetized dogs and immediately frozen in liquid nitrogen. Blood was collected from abdominal aorta and kept on ice. Plasma samples were prepared by centrifugation at 10000 rpm for 10 minutes, 4° C., frozen in liquid nitrogen. Those samples were measured by 4G4/5H10 sandwich ELISA. The result demonstrated that significant decrease in both CSF and plasma sAPPβ concentrations were observed following dosing of BACE1 inhibitor (FIG. 11).

Example 7

Measurement of sAPPβ in Dog CSF and Plasma after Dosing of BACE1 Inhibitor

Figure 12:
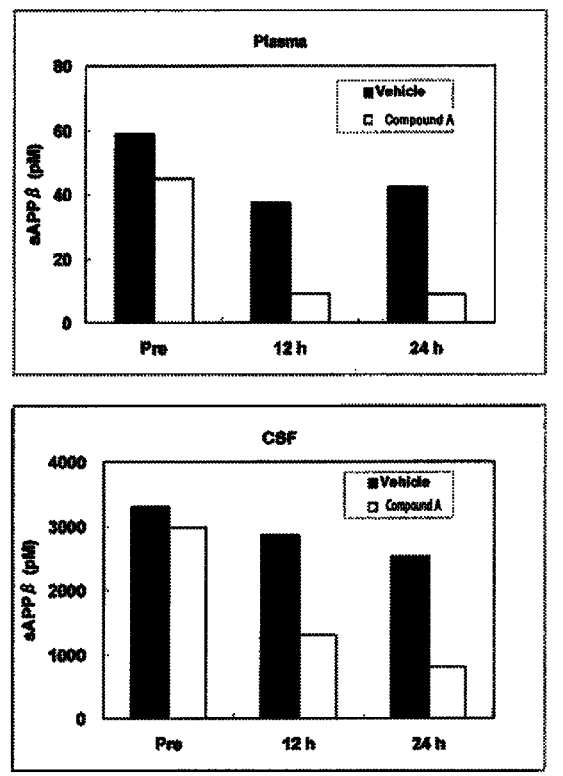
FIG. 12 shows the results of sAPP β in plasma and cerebrospinal fluid of dogs to which were administered BACE1 inhibitors, which were measured by the sandwich ELISA of the 4G4/5H10.

Vehicle (0.5 w/v % methyl cellulose) or 30 mg/15 ml/kg of compound A were orally dosed to 24 or 6-month old beagle dogs (male, 2 each). CSF and plasma samples were collected from these dogs at 24 h after the administration. CSF samples were collected from the cisterna magna of anesthetized dogs and immediately frozen in liquid nitrogen. Blood was collected from cephalic vein or saphenous vein and kept on ice. Plasma samples were prepared by centrifugation at 13000 rpm for 2 minutes, 4° C., frozen in liquid nitrogen. Those samples were measured by 4G4/5H10 sandwich ELISA. The result demonstrated that significant decrease in both CSF and plasma sAPPβ concentrations were observed following dosing of BACE1 inhibitor (FIG. 12).

Example 8

Comparison with the Commercial-Release ELISA Kit

Figure 13:
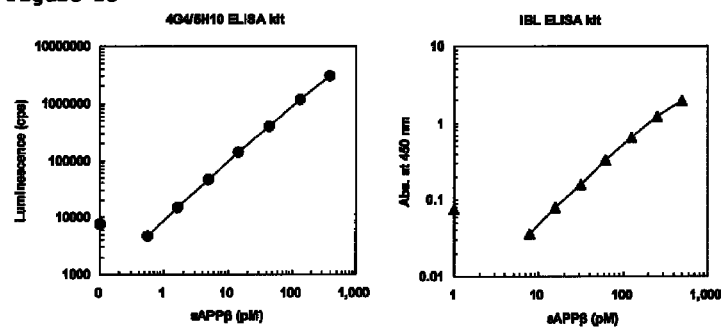
FIG. 13 shows the result of the comparison in standard curves between the sandwich ELISA of the 4G4/5H10 and the sAPP β ELISA kit provided with IBL.
Figure 16:
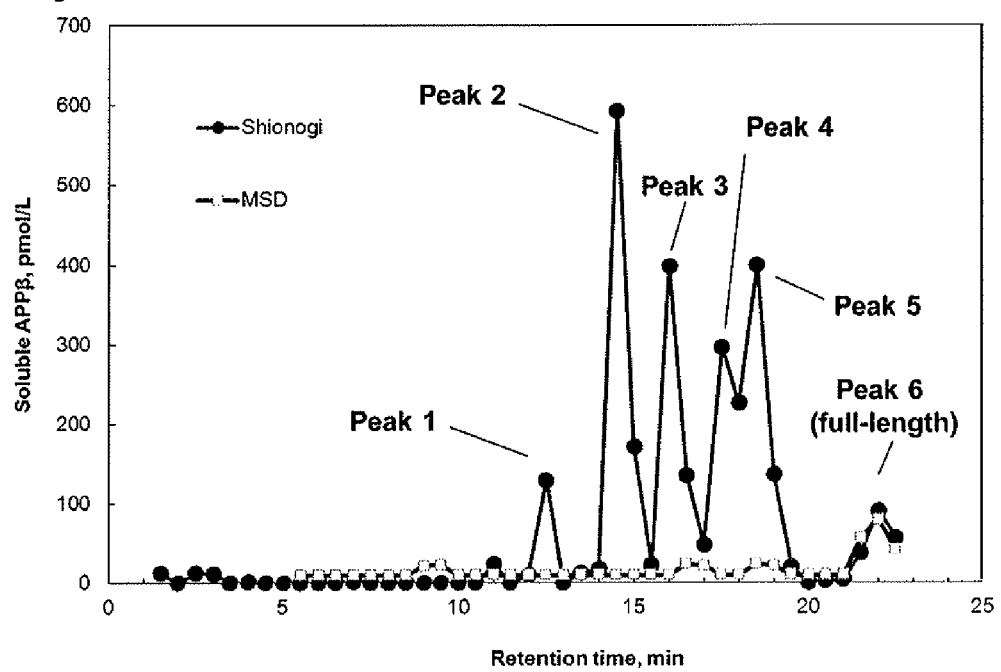
FIG. 16 shows fractions through reverse phase chromatography (RPC) from purified substances obtained from CSF through affinity chromatography with antibody 4G4. FIGure indicates the measured value of sAPP β in each fraction. Horizontal axis indicates retention times (RT) by reverse phase chromatography. Vertical axis indicates the concentration of sAPP β. Fraction with activity is described as peak 1 to 6 according to elution order.

Standard curves were compared between 4G4/5H10 sandwich ELISA and IBL sAPPβ ELISA kit (Cat. No. 27732). In the result the sensitivity of 4G4/5H10 sandwich ELISA is 10 times higher than that of IBL ELISA (FIG. 13).

Example 9

Measurement of sAPPβ in Human Plasma or CSF

The sAPPβ concentrations were measured by above 4G4/5H10 sandwich ELISA methods in 8 human EDTA plasma samples from healthy donors or 6 human CSF samples (Asterand). 5-fold diluted plasma samples and 50-400-fold diluted CSF samples were used. The sAPPβ concentrations of plasma samples and CSF samples were 52.0±11.5 pM (Table 1) and 1000-10000 μM (Table 2), respectively. The ELISA can determine the concentration of sAPPβ in plasma and CSF without a pretreatment accurately. The plasma samples were measured by IBL ELISA kit. Plasma samples were diluted 15-fold for plasma effects. 7 plasma levels were below the lower limit of quantitation. The sAPPβ concentrations of all 2-fold diluted plasma samples by MSD kit were lower than the lower limit of quantitation. The commercial-release ELISA kit could not measure sAPPβ in the plasma samples accurately.

TABLE 1

| Sample No. | sAPPβ level (pM) |
| --- | --- |
| 1 | 67.2 |
| 2 | 50.6 |
| 3 | 42.5 |
| 4 | 35.3 |
| 5 | 53.8 |
| 6 | 46.2 |
| 7 | 68.7 |
| 8 | 51.4 |
| Mean ± SD | 52.0 ± 11.5 |

TABLE 2

| Sample No. | sAPPβ level (pM) |
| --- | --- |
| 1 | 4771 |
| 2 | 1096 |
| 3 | 4401 |
| 4 | 1028 |
| 5 | 2288 |
| 6 | 10475 |

Example 10

Plasma or CSF Separation by Gel Filtration Chromatography

Two-hundred fifty microliters of human plasma or CSF from a single subject was applied directly to TSK-3000SWXL gel filtration columns (TOSOH) arranged in series on an LC-6A HPLC system (SHIMAZU). Eluate was collected as 0.5-mL fractions. The fractions were 10-fold concentrated with a vacuum freeze dryer DRZ350WB (AD-VNTEC). The concentration of sAPPβ in each fractions was measured using foregoing 4G4/5H10 sandwich ELISA or IBL ELISA. The peak was detected in the elution position corresponding to full-length (about 100 kDa) by both ELISA in both case of plasma and CSF. But the peak was appeared in the fragmented elution position (or less 10 kDa) using only 4G4/5H10 sandwich ELISA. The sequence near neoepitope of sAPPβ was identified from the small-size fractions by LC-MS/MS. Therefore, Plasma (FIG. 14a) or CSF (14b) contains a lot of fragmented peptides from sAPPβ, and 4G4/5H10 sandwich ELISA is able to measure the fragmented sAPP β peptides.

Example 11

The Comparison of sAPP β Components in Human CSF Detected by Shionogi sAPP β ELISA or MSD sAPP β ELISA Fifty microliter each of human CSF samples (AD×4, MCI× 4, and Normal×5) was pooled and affinity-purified by anti-sAPP β monoclonal antibody (4G4)-immobilized column.

The column was washed, and the bound proteins were eluted with 100 mM glycine-HCl, pH2.3. Subsequently, the eluate was fractionated into 0.5 mL/tube by reverse-phase chromatography (RPC) with C18 column (YMC-pak ODS-AM, φ 6.0×150 mm) connected to LC-4A system (Shimazu) at a flow-rate of 1.0 mL/min with 0.1% TFA and gradient ACN. The sAPP β concentrations of these fractions were measured by shionogi sAPP β ELISA or MSD sAPP β ELISA, respectively (FIG. 15). Then, we defined the sAPP β peak fractions (from No. 1 to No. 6) in order of earlier retention time of RPC detected by shionogi sAPP β ELISA. MSD sAPP β ELISA recognized only sAPP β peak No. 6 fraction which was considered as the fraction containing a full-length sAPP β (100 kDa). On the other hand, sAPP β peak No. 1-5 fractions were not detected by MSD sAPP β ELISA, resulting that these peaks were considered to contain C-terminal fragments of sAPP β detected by only shionogi sAPP β ELISA.

The sAPP β No. 1-6 fractions were analyzed by LC-MS/MS. In brief, each peak fraction was dried up and dissolved in 8 M urea/0.1% Rapigest SF (Waters)/100 mM triethylammonium bicarbonate (TEAB, pH8.6). Then, reduction and S-carboxyamidomethylation were performed by adding 25 mM dithiothreitol (DTT) at 37° C. for 1 h and by further adding 50 mM iodoacetamide (IAA) at 37° C. for 1 h. After 2-fold dilution, the sAPP β fragments were digested with 1 μg of Lys-C at 37° C. overnight. Subsequently, the digested sAPP β fragments were further digested with 1 μg of Asp-N or 1 μg of Trypsin at 37° C. for 6 h after 4-fold dilution. Then, the solution was desalted by monospin C18 (GL Sciences) according to the manufacturer's instructions, followed by LC-MS/MS analysis. The dried sample was dissolved in 5 μL of 0.1% TFA/5% ACN and was injected into C18 column connected to Easy-nLC 1000 (Thermo Fisher Scientific) at a flow-rate of 300 mL/min with buffer A (0.1% FA) and buffer B (0.1% FA/99.9% ACN). The eluted peptides were directly electrosprayed into Q-exactive hybrid orbitrap mass spectrometry (Thermo Fisher Scientific) with the following parameters: gradient B %; 5-35% (0-10 min), measurement time; 20 min, ion mode; positive, analysis mode; TOP10-ddMS/MS, mass range; m/z 300-1,650, charged ion; 2+, 3+ or 4+, MS resolution; 70,000, MS/MS resolution; 17,500, MS tolerance; 3 ppm, MS/MS tolerance; 0.02 Da. The peptide identification (De novo sequencing) of obtained MS/MS spectra were performed by using PEAKS 6 software (Bioinformatics Solutions) with the following parameters: fixed modification; carbamidomethylation of Cys (+57.02), variable modification; oxidation of Met (+15.99), missed cleavages; 2 (Lys-C/Asp-N) or 1 (Lys-C/Trypsin), non-specific cleavage; one side of the peptide, sAPP β sequence; accession number P05067 [18-671] amyloid beta A4 protein (*Homo sapiens*).

In the sAPP β peak No. 2-6 fractions, the C-terminal fragments of sAPP β were observed, and they possessed epitopes which were recognized by both 5H10 and 4G4 anti-sAPP β monoclonal antibodies in shionogi sAPP β ELISA. In particular, within 57 amino acids sequences from the C-terminal of sAPP β were identified in the sAPP β peak No. 2-4 fractions, suggesting that these fractions were considered to contain many sAPP β C-terminal fragments with their molecular weights smaller than 10 kDa. On the other hand, the N-terminal fragments of sAPP β were identified in the sAPP β peak No. 5 fraction, but this fraction did not show the sAPP β reactivity when MSD sAPP β ELISA was used. These results suggest that the N-terminal (about 100 amino acids as MSD antibody's epitope)-deleted sAPP β truncated forms were contained in the sAPP β peak No. 5 fraction.

Example 12

Sequence Determination of the sAPP β C-Terminal Fragments in Human CSF

The sAPP β peak No. 2 and No. 3 fractions were analyzed by LC-MS/MS. The sAPP β peak No. 2 fraction was performed by intact analysis. While, the sAPP β peak No. 3 fraction was performed by digestion analysis.

In intact analysis, the sAPP β No. 2 fraction was directly analyzed by LC-MS/MS. In brief, the dried sample was dissolved in 5 μL of 0.1% TFA/5% ACN and was injected into C18 column connected to Easy-nLC 1000 at a flow-rate of 300 mL/min with buffer A (0.1% FA) and buffer B (0.1% FA/99.9% ACN). The eluted peptides were directly electrosprayed into Q-exactive hybrid orbitrap mass spectrometry with the following parameters: gradient B %; 5-35% (0-10 min), measurement time; 20 min, ion mode; positive, analysis mode; TOP10-ddMS/MS, mass range; m/z 300-1,650, charged ion; 2+, 3+, 4+, 5+, 6+, 7+, 8+ or >8+, MS resolution; 70,000, MS/MS resolution; 17,500, MS tolerance; 3 ppm, MS/MS tolerance; 0.02 Da. The peptide identification (De novo sequencing) of obtained MS/MS spectra were performed by using PEAKS 6 software with the following parameters: variable modification; oxidation of Met (+15.99), sAPP β sequence; accession number P05067 [18-671] amyloid beta A4 protein (*Homo sapiens*).

In digestion analysis, the sAPP β No. 3 fraction was analyzed by LC-MS/MS as described in the section of Example 11.

Consequently, the intact analysis of the sAPP β peak No. 2 fraction revealed that this fraction is containing 8 novel sAPP β C-terminal fragments (25, 26, 36, 39, 45, 47, 48 and 49 mer, FIG. 17). On the other hand, the digestion analysis of the sAPP β peak No. 3 fraction revealed that 1 novel sAPP β C-terminal fragment (57 mer) exist (FIG. 17).

Example 13

The Comparison of sAPP β Concentration in Human CSF Between Shionogi sAPP β ELISA and MSD sAPP β ELISA We purchased human CSF from 5 patients with AD assessed by MMSE test, and compared the measurement values of sAPP β concentrations between MSD sAPP β ELISA (for full-length sAPP β only) and shionogi (4G4/5H10) sAPP β ELISA (for the sum of full-length sAPP β and C-terminal fragments). The procedures of Shionogi sAPP β ELISA was followed by the section of Example 4. While, MSD sAPP β ELISA was performed by manufacturer's protocol. The protein standard was used in accessory of MSD sAPP β ELISA kit whichever ELISA was used. Consequently, the total sAPP β concentration (full-length and C-terminal fragments) by shionogi sAPP β ELISA could be detected by 7-fold higher compared to MSD sAPP β ELISA (FIG. 18). And the amounts of full-length sAPP β were estimated as 14.5%, suggesting that a lot of sAPP β C-terminal fragments exist more than full-length form in CSF. This result was not conflict with the measurement values by shionogi sAPP β ELISA of CSF fraction by SEC (claim 10, FIG. 14b), suggesting that the fragments of sAPP β were predominantly existed in CSF.

The invention claimed is:

1. A monoclonal antibody raised against soluble amyloid precursor protein β (sAPP β) or an antigen binding fragment thereof which specifically binds to the amino acid sequence of SEQ ID NO: 37 within sAPP β, wherein the monoclonal antibody comprises a heavy chain variable region having the amino acid sequence of SEQ ID NO: 14 and a light chain variable region having the amino acid sequence of SEQ ID NO: 15.

2. A method for quantifying sAPP β comprising: contacting a sample with the monoclonal antibody or antigen binding fragment of claim 1; determining if said antibody binds to sAPP β in said sample and quantifying bound sAPP β.

3. A method for determining whether a patient has a disease related to sAPP β comprising: contacting a sample from the patient with the monoclonal antibody or antigen binding fragment of claim 1; and determining if said antibody binds to a component of said sample, wherein the presence of sAPP β binding indicates that the patient has the disease.

4. A method for screening for an inhibitor of beta secretase 1 (BACE1) comprising: contacting BACE1 and APP with a test substance, adding the monoclonal antibody or antigen binding fragment of claim 1 to evaluate an amount of sAPP β;

and determining the test substance as a BACE1 inhibitor when the amount of sAPP β is less as compared to that in absence of the test substance.

5. A monoclonal antibody against sAPP β or an antigen binding fragment thereof comprising: a heavy chain variable region having the amino acid sequence of SEQ ID NO: 14 and a light chain variable region having the amino acid sequence of SEQ ID NO: 15.

6. A method for quantifying sAPP β comprising: contacting a sample with the monoclonal antibody or antigen binding fragment of claim 5; determining if said antibody binds to sAPP β in said sample and quantifying bound sAPP β.

7. A method for determining whether a patient has a disease related to sAPP β comprising: contacting a sample from the patient with the monoclonal antibody or antigen binding fragment of claim 5; and determining if said antibody binds to a component of said sample, wherein the presence of sAPP β binding indicates that the patient has the disease.

8. A monoclonal antibody against sAPP β or an antigen binding fragment thereof comprising: a heavy chain variable region comprising a complementarity determining region (CDR) 1 consisting of SEQ ID NO: 22, a CDR 2 consisting of SEQ ID NO: 23 and a CDR 3 consisting of SEQ ID NO: 24 and a light chain variable region comprising a CDR 1 consisting of SEQ ID NO: 25, a CDR 2 consisting of SEQ ID NO: 26 and a CDR 3 consisting of SEQ ID NO: 27.

9. A method for quantifying sAPP β comprising: contacting a sample with the monoclonal antibody or antigen binding fragment of claim 8; determining if said antibody binds to sAPP β in said sample and quantifying bound sAPP β.

10. A method for determining whether a patient has a disease related to sAPP β comprising: contacting a sample from the patient with the monoclonal antibody or antigen binding fragment of claim 8; and determining if said antibody binds to a component of said sample, wherein the presence of sAPP β binding indicates that the patient has the disease.

11. A kit including the monoclonal antibody or antigen binding fragment of claim 8.

\* \* \* \* \*

SEQUENCE LISTING

<160> NUMBER OF SEQ ID NOS: 37

<210> SEQ ID NO 1
<211> LENGTH: 9
<212> TYPE: PRT
<213> ORGANISM: Artificial Sequence
<220> FEATURE:
<223> OTHER INFORMATION: Peptide

<400> SEQUENCE: 1

Thr Glu Glu Ile Ser Glu Val Lys Met
1               5

<210> SEQ ID NO 2
<211> LENGTH: 10
<212> TYPE: PRT
<213> ORGANISM: Artificial Sequence
<220> FEATURE:
<223> OTHER INFORMATION: peptide

<400> SEQUENCE: 2

Cys Thr Glu Glu Ile Ser Glu Val Lys Met
1               5                   10

<210> SEQ ID NO 3
<211> LENGTH: 10
<212> TYPE: PRT
<213> ORGANISM: Artificial Sequence
<220> FEATURE:
<223> OTHER INFORMATION: peptide

<400> SEQUENCE: 3

Thr Glu Glu Ile Ser Glu Val Lys Met Asp
1               5                   10

<210> SEQ ID NO 4
<211> LENGTH: 8
<212> TYPE: PRT
<213> ORGANISM: Artificial Sequence
<220> FEATURE:
<223> OTHER INFORMATION: peptide

<400> SEQUENCE: 4

Thr Glu Glu Ile Ser Glu Val Lys
1               5

<210> SEQ ID NO 5
<211> LENGTH: 34
<212> TYPE: PRT
<213> ORGANISM: Artificial Sequence
<220> FEATURE:
<223> OTHER INFORMATION: peptide

<400> SEQUENCE: 5

Asp Ser Val Pro Ala Asn Thr Glu Asn Glu Val Glu Pro Val Asp Ala
1               5                   10                  15

Arg Pro Ala Ala Asp Arg Gly Leu Thr Thr Arg Pro Gly Ser Gly Leu
            20                  25                  30

Thr Asn

<210> SEQ ID NO 6
<211> LENGTH: 35
<212> TYPE: PRT
<213> ORGANISM: Artificial Sequence
<220> FEATURE:
<223> OTHER INFORMATION: peptide

```
<400> SEQUENCE: 6

Asp Ser Val Pro Ala Asn Thr Glu Asn Glu Val Glu Pro Val Asp Ala
1               5                   10                  15

Arg Pro Ala Ala Asp Arg Gly Leu Thr Thr Arg Pro Gly Ser Gly Leu
            20                  25                  30

Thr Asn Cys
        35

<210> SEQ ID NO 7
<211> LENGTH: 45
<212> TYPE: PRT
<213> ORGANISM: Artificial Sequence
<220> FEATURE:
<223> OTHER INFORMATION: peptide

<400> SEQUENCE: 7

Asp Ser Val Pro Ala Asn Thr Glu Asn Glu Val Glu Pro Val Asp Ala
1               5                   10                  15

Arg Pro Ala Ala Asp Arg Gly Leu Thr Thr Arg Pro Gly Ser Gly Leu
            20                  25                  30

Thr Asn Ile Lys Thr Glu Glu Ile Ser Glu Val Lys Met
        35                  40                  45

<210> SEQ ID NO 8
<211> LENGTH: 12
<212> TYPE: PRT
<213> ORGANISM: Artificial Sequence
<220> FEATURE:
<223> OTHER INFORMATION: peptide

<400> SEQUENCE: 8

Asp Ser Val Pro Ala Asn Thr Glu Asn Glu Val Glu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: peptide

<400> SEQUENCE: 9

Asn Glu Val Glu Pro Val Asp Ala Arg Pro Ala Ala
1               5                   10

<210> SEQ ID NO 10
<211> LENGTH: 12
<212> TYPE: PRT
<213> ORGANISM: Artificial Sequence
<220> FEATURE:
<223> OTHER INFORMATION: peptide

<400> SEQUENCE: 10

Arg Pro Ala Ala Asp Arg Gly Leu Thr Thr Arg Pro
1               5                   10

<210> SEQ ID NO 11
<211> LENGTH: 10
<212> TYPE: PRT
<213> ORGANISM: Artificial Sequence
<220> FEATURE:
<223> OTHER INFORMATION: peptide

<400> SEQUENCE: 11
```

```
Thr Thr Arg Pro Gly Ser Gly Leu Thr Asn
 1               5                  10
```

<210> SEQ ID NO 12
<211> LENGTH: 118
<212> TYPE: PRT
<213> ORGANISM: Artificial Sequence
<220> FEATURE:
<223> OTHER INFORMATION: VH of antibody 4G4

<400> SEQUENCE: 12

```
Glu Met Lys Leu Val Glu Ser Gly Gly Gly Leu Val Glu Pro Gly Gly
 1               5                  10                  15

Ser Leu Lys Leu Ser Cys Ala Ala Ser Gly Phe Thr Phe Ser Asn Tyr
                20                  25                  30

Ala Met Ser Trp Val Arg Gln Thr Pro Asp Lys Arg Leu Glu Trp Val
            35                  40                  45

Ala Ser Ile Gly Arg Gly Gly Ser Thr Phe Tyr Pro Asp Ser Val Lys
        50                  55                  60

Gly Arg Phe Thr Ile Ser Arg Asp Arg Val Arg Asn Ile Leu Tyr Leu
65                  70                  75                  80

Gln Met Asn Ser Leu Arg Ser Glu Asp Thr Ala Ile Tyr Tyr Cys Arg
                85                  90                  95

Val Ile Tyr Ser Gln Ser Ile Ser Phe Asp Tyr Trp Gly Gln Gly Thr
            100                 105                 110

Thr Leu Thr Val Ser Ser
        115
```

<210> SEQ ID NO 13
<211> LENGTH: 114
<212> TYPE: PRT
<213> ORGANISM: Artificial Sequence
<220> FEATURE:
<223> OTHER INFORMATION: VL of antibody 4G4

<400> SEQUENCE: 13

```
Asp Val Val Leu Thr Gln Thr Pro Leu Thr Leu Ser Val Thr Ile Gly
 1               5                  10                  15

Gln Pro Ala Ser Ile Ser Cys Lys Ser Arg Gln Ser Leu Leu Asp Ser
                20                  25                  30

Asp Gly Lys Thr Tyr Leu His Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Phe Thr Phe Gly Ser Gly Thr Lys Leu Glu Ile Lys
            100                 105                 110

Arg Ala
```

<210> SEQ ID NO 14
<211> LENGTH: 117
<212> TYPE: PRT
<213> ORGANISM: Artificial Sequence
<220> FEATURE:
<223> OTHER INFORMATION: VH of antibody 5H10

```
<400> SEQUENCE: 14

Gln Val Gln Leu Gln Gln Ser Gly Thr Glu Leu Ala Lys Pro Gly Ala
1               5                   10                  15

Ser Val Lys Met Ser Cys Lys Ala Ser Gly Tyr Thr Phe Ile Asp Tyr
            20                  25                  30

Trp Met His Trp Ile Lys Gln Ser Pro Gly Gln Gly Leu Glu Trp Ile
        35                  40                  45

Gly Phe Ile Asn Pro Arg Ser Gly Ser Thr Thr Tyr Asn Gln Lys Phe
    50                  55                  60

Arg Asp Lys Ala Thr Leu Thr Val Asp Thr Ser Ser Ser Thr Ala Tyr
65                  70                  75                  80

Met Gln Leu Thr Ser Leu Thr Ser Glu Asp Ser Ala Val Tyr Tyr Cys
                85                  90                  95

Thr Arg Pro Asp Phe Asp Tyr Phe Asp Tyr Trp Gly Gln Gly Thr Thr
            100                 105                 110

Leu Thr Val Ser Ser
        115

<210> SEQ ID NO 15
<211> LENGTH: 114
<212> TYPE: PRT
<213> ORGANISM: Artificial Sequence
<220> FEATURE:
<223> OTHER INFORMATION: VL of antibody 5H10

<400> SEQUENCE: 15

Asp Val Leu Met Thr Gln Thr Pro Leu Ser Leu Pro Val Ser Leu Gly
1               5                   10                  15

Asp His Ala Ser Ile Ser Cys Arg Ser Ser Gln Ser Ile Val Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Ile Tyr Tyr Cys Phe Gln Ala
                85                  90                  95

Ser His Val Pro Leu Thr Phe Gly Ala Gly Thr Lys Leu Glu Leu Lys
            100                 105                 110

Arg Ala

<210> SEQ ID NO 16
<211> LENGTH: 5
<212> TYPE: PRT
<213> ORGANISM: Artificial Sequence
<220> FEATURE:
<223> OTHER INFORMATION: CDR1 of 4G4 heavy chain

<400> SEQUENCE: 16

Asn Tyr Ala Met Ser
1               5

<210> SEQ ID NO 17
<211> LENGTH: 16
<212> TYPE: PRT
<213> ORGANISM: Artificial Sequence
<220> FEATURE:
<223> OTHER INFORMATION: CDR2 of 4G4 heavy chain
```

```
<400> SEQUENCE: 17

Ser Ile Gly Arg Gly Gly Ser Thr Phe Tyr Pro Asp Ser Val Lys Gly
1               5                   10                  15

<210> SEQ ID NO 18
<211> LENGTH: 10
<212> TYPE: PRT
<213> ORGANISM: Artificial Sequence
<220> FEATURE:
<223> OTHER INFORMATION: CDR3 of 4G4 heavy chain

<400> SEQUENCE: 18

Ile Tyr Ser Gln Ser Ile Ser Phe Asp Tyr
1               5                   10

<210> SEQ ID NO 19
<211> LENGTH: 16
<212> TYPE: PRT
<213> ORGANISM: Artificial Sequence
<220> FEATURE:
<223> OTHER INFORMATION: CDR1 of 4G4 light chain

<400> SEQUENCE: 19

Lys Ser Arg Gln Ser Leu Leu Asp Ser Asp Gly Lys Thr Tyr Leu His
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: CDR2 of 4G4 light chain

<400> SEQUENCE: 20

Leu Val Ser Lys Leu Asp Ser
1               5

<210> SEQ ID NO 21
<211> LENGTH: 9
<212> TYPE: PRT
<213> ORGANISM: Artificial Sequence
<220> FEATURE:
<223> OTHER INFORMATION: CDR3 of 4G4 light chain

<400> SEQUENCE: 21

Trp Gln Gly Thr His Phe Pro Phe Thr
1               5

<210> SEQ ID NO 22
<211> LENGTH: 5
<212> TYPE: PRT
<213> ORGANISM: Artificial Sequence
<220> FEATURE:
<223> OTHER INFORMATION: CDR1 of 5H10 heavy chain

<400> SEQUENCE: 22

Asp Tyr Trp Met His
1               5

<210> SEQ ID NO 23
<211> LENGTH: 17
<212> TYPE: PRT
<213> ORGANISM: Artificial Sequence
<220> FEATURE:
<223> OTHER INFORMATION: CDR2 of 5H10 heavy chain
```

```
<400> SEQUENCE: 23

Phe Ile Asn Pro Arg Ser Gly Ser Thr Thr Tyr Asn Gln Lys Phe Arg
1               5                   10                  15

Asp

<210> SEQ ID NO 24
<211> LENGTH: 8
<212> TYPE: PRT
<213> ORGANISM: Artificial Sequence
<220> FEATURE:
<223> OTHER INFORMATION: CDR3 of 5H10 heavy chain

<400> SEQUENCE: 24

Pro Asp Phe Asp Tyr Phe Asp Tyr
1               5

<210> SEQ ID NO 25
<211> LENGTH: 16
<212> TYPE: PRT
<213> ORGANISM: Artificial Sequence
<220> FEATURE:
<223> OTHER INFORMATION: CDR1 of 5H10 light chain

<400> SEQUENCE: 25

Arg Ser Ser Gln Ser Ile Val Gln Ser Asn Gly Asn Thr Tyr Leu Glu
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: CDR2 of 5H10 light chain

<400> SEQUENCE: 26

Lys Val Ser Asn Arg Phe Ser
1               5

<210> SEQ ID NO 27
<211> LENGTH: 9
<212> TYPE: PRT
<213> ORGANISM: Artificial Sequence
<220> FEATURE:
<223> OTHER INFORMATION: CDR3 of 5H10 light chain

<400> SEQUENCE: 27

Phe Gln Ala Ser His Val Pro Leu Thr
1               5

<210> SEQ ID NO 28
<211> LENGTH: 25
<212> TYPE: PRT
<213> ORGANISM: Homo sapiens

<400> SEQUENCE: 28

Asp Arg Gly Leu Thr Thr Arg Pro Gly Ser Gly Leu Thr Asn Ile Lys
1               5                   10                  15

Thr Glu Glu Ile Ser Glu Val Lys Met
            20                  25

<210> SEQ ID NO 29
<211> LENGTH: 26
<212> TYPE: PRT
<213> ORGANISM: Homo sapiens
```

```
<400> SEQUENCE: 29

Ala Asp Arg Gly Leu Thr Thr Arg Pro Gly Ser Gly Leu Thr Asn Ile
1               5                   10                  15

Lys Thr Glu Glu Ile Ser Glu Val Lys Met
            20                  25

<210> SEQ ID NO 30
<211> LENGTH: 36
<212> TYPE: PRT
<213> ORGANISM: Homo sapiens

<400> SEQUENCE: 30

Glu Val Glu Pro Val Asp Ala Arg Pro Ala Ala Asp Arg Gly Leu Thr
1               5                   10                  15

Thr Arg Pro Gly Ser Gly Leu Thr Asn Ile Lys Thr Glu Glu Ile Ser
            20                  25                  30

Glu Val Lys Met
        35

<210> SEQ ID NO 31
<211> LENGTH: 39
<212> TYPE: PRT
<213> ORGANISM: Homo sapiens

<400> SEQUENCE: 31

Thr Glu Asn Glu Val Glu Pro Val Asp Ala Arg Pro Ala Ala Asp Arg
1               5                   10                  15

Gly Leu Thr Thr Arg Pro Gly Ser Gly Leu Thr Asn Ile Lys Thr Glu
            20                  25                  30

Glu Ile Ser Glu Val Lys Met
        35

<210> SEQ ID NO 32
<211> LENGTH: 45
<212> TYPE: PRT
<213> ORGANISM: Homo sapiens

<400> SEQUENCE: 32

Asp Ser Val Pro Ala Asn Thr Glu Asn Glu Val Glu Pro Val Asp Ala
1               5                   10                  15

Arg Pro Ala Ala Asp Arg Gly Leu Thr Thr Arg Pro Gly Ser Gly Leu
            20                  25                  30

Thr Asn Ile Lys Thr Glu Glu Ile Ser Glu Val Lys Met
            35                  40                  45

<210> SEQ ID NO 33
<211> LENGTH: 47
<212> TYPE: PRT
<213> ORGANISM: Homo sapiens

<400> SEQUENCE: 33

Gly Ala Asp Ser Val Pro Ala Asn Thr Glu Asn Glu Val Glu Pro Val
1               5                   10                  15

Asp Ala Arg Pro Ala Ala Asp Arg Gly Leu Thr Thr Arg Pro Gly Ser
            20                  25                  30

Gly Leu Thr Asn Ile Lys Thr Glu Glu Ile Ser Glu Val Lys Met
            35                  40                  45

<210> SEQ ID NO 34
<211> LENGTH: 48
```

```
<212> TYPE: PRT
<213> ORGANISM: Homo sapiens

<400> SEQUENCE: 34

Phe Gly Ala Asp Ser Val Pro Ala Asn Thr Glu Asn Glu Val Glu Pro
1               5                   10                  15

Val Asp Ala Arg Pro Ala Ala Asp Arg Gly Leu Thr Thr Arg Pro Gly
                20                  25                  30

Ser Gly Leu Thr Asn Ile Lys Thr Glu Glu Ile Ser Glu Val Lys Met
            35                  40                  45

<210> SEQ ID NO 35
<211> LENGTH: 49
<212> TYPE: PRT
<213> ORGANISM: Homo sapiens

<400> SEQUENCE: 35

Ser Phe Gly Ala Asp Ser Val Pro Ala Asn Thr Glu Asn Glu Val Glu
1               5                   10                  15

Pro Val Asp Ala Arg Pro Ala Ala Asp Arg Gly Leu Thr Thr Arg Pro
                20                  25                  30

Gly Ser Gly Leu Thr Asn Ile Lys Thr Glu Glu Ile Ser Glu Val Lys
            35                  40                  45

Met

<210> SEQ ID NO 36
<211> LENGTH: 57
<212> TYPE: PRT
<213> ORGANISM: Homo sapiens

<400> SEQUENCE: 36

Leu Asp Asp Leu Gln Pro Trp His Ser Phe Gly Ala Asp Ser Val Pro
1               5                   10                  15

Ala Asn Thr Glu Asn Glu Val Glu Pro Val Asp Ala Arg Pro Ala Ala
                20                  25                  30

Asp Arg Gly Leu Thr Thr Arg Pro Gly Ser Gly Leu Thr Asn Ile Lys
            35                  40                  45

Thr Glu Glu Ile Ser Glu Val Lys Met
        50                  55

<210> SEQ ID NO 37
<211> LENGTH: 16
<212> TYPE: PRT
<213> ORGANISM: Homo sapiens

<400> SEQUENCE: 37

Asp Arg Gly Leu Thr Thr Arg Pro Gly Ser Gly Leu Thr Asn Ile Lys
1               5                   10                  15
```